(12) United States Patent
Sohn et al.

(10) Patent No.: US 10,584,214 B2
(45) Date of Patent: *Mar. 10, 2020

(54) CATIONIC POLYPHOSPHAZENE COMPOUND, POLYPHOSPHAZENES-DRUG CONJUGATE COMPOUND AND METHOD FOR PREPARING SAME

(71) Applicant: CNPHARM CO., LTD., Seoul (KR)

(72) Inventors: Youn Soo Sohn, Seoul (KR); Yong Joo Jun, Seoul (KR); Prakash Gouda Avaji, Seoul (KR)

(73) Assignee: CNPHARM CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/430,230

(22) Filed: Jun. 3, 2019

(65) Prior Publication Data
US 2019/0284345 A1    Sep. 19, 2019

Related U.S. Application Data

(63) Continuation of application No. 15/125,543, filed as application No. PCT/KR2015/002488 on Mar. 13, 2015, now Pat. No. 10,336,867.

(30) Foreign Application Priority Data

Mar. 14, 2014  (KR) .................. 10-2014-0030564
Mar. 11, 2015  (KR) .................. 10-2015-0034030

(51) Int. Cl.
| *C08G 79/025* | (2016.01) |
| *A61K 47/58* | (2017.01) |
| *A61K 47/60* | (2017.01) |
| *C08G 81/00* | (2006.01) |
| *A61K 31/555* | (2006.01) |
| *A61K 31/4745* | (2006.01) |
| *A61K 31/337* | (2006.01) |

(52) U.S. Cl.
CPC .......... *C08G 79/025* (2013.01); *A61K 31/337* (2013.01); *A61K 31/4745* (2013.01); *A61K 31/555* (2013.01); *A61K 47/60* (2017.08); *A61K 47/605* (2017.08); *C08G 81/00* (2013.01)

(58) Field of Classification Search
CPC ... C08G 79/025; A61K 47/605; A61K 31/337
See application file for complete search history.

(56) References Cited

U.S. PATENT DOCUMENTS 10,336,867 B2 *  7/2019  Sohn .................... C08G 79/025
2013/0324490 A1   12/2013  Teasdale

FOREIGN PATENT DOCUMENTS

WO    2007/145455 A1    12/2007

OTHER PUBLICATIONS

Office Action dated Mar. 8, 2019 for related CN Patent Application No. 201580026199.8, in 7 pages.
Yong Joo Jun et al., "Selective tumor targeting by enhanced permeability and retention effect. Synthesis and antitumor activity of polyphosphazene—platinum (II) con," Journal of Inorganic Biochemistry 99 (2005) 1593-1601.

* cited by examiner

*Primary Examiner* — Mark S Kaucher
(74) *Attorney, Agent, or Firm* — Procopio, Cory, Hargreaves & Savitch LLP

(57) ABSTRACT

The present invention relates to a new class of cationic linear polyphosphazenes bearing as side groups a hydrophilic poly(ethylene glycol) and a spacer group selected from the group consisting of lysine, oligopeptides containing lysine, amino-ethanol, amino-propanol, amino-butanol, amino-pentanol and amino-hexanol, and the polyphosphazene-drug conjugates comprising hydrophobic anticancer drugs by covalent bonding and the preparation methods thereof. The present polyphosphazene-drug conjugates exhibit outstanding tumor selectivity and low toxicity.

1 Claim, 7 Drawing Sheets

CATIONIC POLYPHOSPHAZENE COMPOUND, POLYPHOSPHAZENES-DRUG CONJUGATE COMPOUND AND METHOD FOR PREPARING SAME

CROSS-REFERENCE TO RELATED APPLICATIONS

This application is a continuation of U.S. application Ser. No. 15/125,543, filed Oct. 20, 2016, which is incorporated herein by reference in its entirety for all purposes.

TECHNICAL FIELD

The present invention relates to highly tumor selective and biocompatible cationic linear polyphosphazene carrier polymers and their anticancer drug conjugates, and a preparation method thereof.

BACKGROUND ART

Most of the anticancer drugs currently in clinical use for chemotherapy are monomeric compounds with a low molecular weight less than 1000 Da. Such monomeric low molecular weight anticancer drugs are well known to cause severe toxicities and side effects due to their non-selectivity to tumor cells and tissue when injected intravenously, and furthermore, their short half-life less than a few hours during blood circulation limits their sustainable efficacy. Therefore, the most critical key technologies to overcome in the new anticancer drug development is the tumor targeting technology for selective delivery of anticancer drugs to the tumor site and timely releasing technology of the active component of anticancer drugs in the tumor site. A great deal of efforts to overcome such limits have been made in the world for last decades, and as a result, it has been discovered that polymeric drug delivery systems are one of the most efficient and practical ways to bring a breakthrough, from which a new field called "polymer therapy" emerged (R. Haag, F. Kratz, *Angew. Chem. Int. Ed.* 45 (2006) 1198-1215).

Most of the polymers employed as drug delivery systems are organic polymers synthetic or natural. Numerous natural and synthetic polymers were attempted as drug delivery systems for polymer therapy, but only a limited number of drug delivery systems were found to be useful, since in addition to afore-mentioned tumor targeting properties and releasing kinetics many requirements such as water solubility, biodegradability, self-toxicity, compatibility with the loaded drug should be satisfied for polymer therapy of cancer.

The present inventors discovered decades ago that in contrast to the organic polymers above-mentioned a new class of organic/inorganic hybrid polymers were designed by grafting various organic groups to the inorganic polymer backbone consisting of alternating nitrogen and phosphorus atoms called phospphazene (Y. S. Sohn, et al. *Macromolecules*, 1995, 28, 7566), which have been intensively developed as drug delivery systems for cancer therapy. In the early stage, various hydrophilic poly(ethylene glycol) (PEG) and hydrophobic oligopeptides were introduced into the phosphazene backbone to obtain amphiphilic polyphosphazenes affording thermosensitive drug delivery systems. It was also found that such amphiphilic polyphosphazenes are self-assembled into various nanostructures such as thermosensitive micelles and hydrogels useful for drug delivery in aqueous solution, but also were observed decreased water solubility and some toxicity due to some hydrophobic oligopeptide grafted to polyphosphazene backbone. It is generally known that such amphiphilic polymers exhibit a lower critical solution temperature (LCST) at which the polymer start to precipitate from its aqueous solution when slowly heated. Therefore, amphiphilic polymer drug delivery system should exhibit higher LCST than body temperature for intravenous injection to avoid its precipitation during blood circulation.

Concerning the hydrophobic anticancer drugs, the taxane family including paclitaxel and docetaxel is one of the most widely used for efficient chemotherapy of a wide spectrum of cancers including breast, ovarian and non-small cell lung cancers. Since these taxane anticancer agents are only slightly soluble in water (<1 μg/ml), they cannot be directly injected but should be formulated using surfactants such as Polysorbate 80 or Cremophore EL and ethanol for IV injection. However, such formulated taxane anticancer agents exhibit several adverse effects including neurotoxicity and neutropenia due to the agent itself and hypersensitivity due to the solvent system, which limit their wider clinical use.

Therefore, a great deal of researches have been made in various fields during the last decade to overcome such adverse effects, and among them, nanotechnology using various structural morphology is most actively progressing. In particular, the polymeric micelles composed of the hydrophilic outer shell and hydrophobic core can afford to solubilize the hydrophobic anticancer drugs such as taxane by encapsulation of the hydrophobic drug molecules in the hydrophobic micelle core. Also, the taxane drug molecules may be conjugated by chemical bonding to the hydrophilic poly(ethylene glycol) to solubilize, which are now in clinical trials.

Such polymeric prodrugs composed of small molecular anticancer drugs conjugated to the polymeric drug delivery systems are expected to extend their blood circulation time and afford tumor targeting properties by enhanced permeability and retention (EPR) effect (H. Maeda et al. *J. Control. Release* 65(2000) 271-284) along with controlled drug release, resulting in maximum drug efficacy and minimum toxicity. According to the recent reports, the polymer particle size should be in the range of 50-200 nm in order to exhibit tumor targeting properties by EPR effect (V. P. Torchilin, *J. Control. Release* 73 (2001) 137-172). Also, it was reported from the study of gene delivery that cationic polymers can easily permeate anionic tumor cells (N. P. Gabrielson, D. W. Park, *J. Control. Release* 136 (2009) 54-61). However, Poliglumex composed of paclitaxel conjugated to poly(glutamic acid) currently in clinical phase III is strongly cationic but it was known to be more accumulated in other organs than in tumor tissue, which delays its commercialization (S. Wallace; C. Li, *Adv. Drug Deliv. Rev.* 60 (2008) 886-898).

PRIOR ART DOCUMENT

[Non patent document 1]
R. Haag, F. Kratz, *Angew. Chem. Int. Ed.* 45(2006)1198-1215)

DISCLOSURE

Technical Problem

Therefore, it is an object of the present invention to provide a novel class of cationic polyphosphazene compounds for drug delivery and their anticancer drug conjugate compounds with excellent tumor selectivity and easy drug releasing properties in the tumor site, and a preparation method thereof.

The present inventors have been searching clinically more efficient drug delivery systems affording excellent tumor selectivity and easy drug releasing properties under the above-mentioned technical background and finally discovered that polyphosphazenes grafted with a hydrophilic PEG as solubilizing group and one selected from a multifunctional amino acid, an oligopeptide involving amino acid or linear amino alcohol as spacer group to conjugate with an hydrophobic anticancer drug exhibit excellent tumor selectivity due to their cationic properties and long blood circulation. The present inventors have further found that when the hydrophobic anticancer drugs are conjugated to the above-mentioned polyphosphazene carrier polymer by using an acid cleavable linker, smart polymeric anticancer drugs with excellent tumor selectivity and controlled releasing properties in the tumor site by acid degradation are obtained.

Technical Solution

In order to accomplish the above task, the present invention provides the linear polyphosphazenes represented by the following chemical formula 1.

[Chemical formula 1]

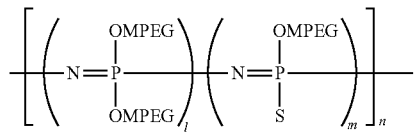

wherein n is an integer from 1 to 300; MPEG represents methoxy poly(ethylene glycol) with a molecular weight of 350 to 1000; S is a space group selected from the group consisting of lysine, arginine, glutamine, asparagine, tyrosine, lysine containing oligopeptide, arginine containing oligopeptide, glutamine containing oligopeptide, asparagine containing oligopeptide, tyrosine containing oligopeptide, amino-ethanol, amino-propanol, amino-butanol, amino-pentanol, and amino-hexanol; 1 equals to 0~0.9; m equals to 0.1~1 and 1+m equals to 1.

The present invention also provides the polyphosphazene-anticancer drug conjugates represented by the following chemical formula 2.

[Chemical formula 2]

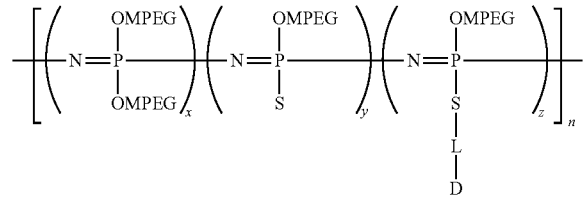

wherein n is an integer from 1 to 300; MPEG represents methoxy poly(ethylene glycol) with a molecular weight of 350 to 1000; S is a space group selected from the group consisting of lysine, arginine, glutamine, asparagine, tyrosine, lysine containing oligopeptide, arginine containing oligopeptide, glutamine containing oligopeptide, asparagine containing oligopeptide, tyrosine containing oligopeptide, amino-ethanol, amino-propanol, amino-butanol, amino-pentanol, and amino-hexanol; L is a linker to connect the spacer group of the polymer and drug molecule D bearing hydroxyl or amine group; x and y are independently in the range of 0~0.5; z is in the range of 0~1; and x+y+z=1.

Also, the present invention provides a method of preparing polyphosphazene-drug conjugate compounds represented by the chemical formula 2 comprising the steps (a) to (d):
(a) preparing a PEGylated polyphosphazene intermediate by subjecting a starting material hexachlorocyclotriphosphazene to thermal polymerization to obtain a linear poly (dichlorophosphazene) and then reacting the linear poly (dichlorophosphazene) with the sodium salt of methoxy poly(ethylene glycol),
(b) preparing a hydrophilic cationic polyphosphazene carrier polymer by reacting the PEGylated polyphosphazene intermediate with a space group selected from the group consisting of lysine ester, lysine containing oligopeptide ester, amino-ethanol, amino-propanol, amino-butanol, amino-pentanol, and amino-hexanol,
(c) preparing a drug-linker precursor by reacting a drug molecules bearing OH or $NH_2$ functional group with an appropriate linker,
(d) connecting the drug-linker precursor obtained from the Step (c) to the space group of the hydrophilic cationic polyphosphazene carrier polymer obtained from the Step (b).

Alternatively, the present invention provides a method of preparing polyphosphazene-drug conjugate compounds represented by the following chemical formula 2 comprising the steps (a) to (d):
(a) preparing a PEGylated polyphosphazene intermediate by subjecting a starting material hexachlorocyclotriphosphazene to thermal polymerization to obtain a linear poly (dichlorophosphazene) and then reacting the linear poly (dichlorophosphazene) with the sodium salt of methoxy poly(ethylene glycol),
(b) preparing a hydrophilic cationic polyphosphazene carrier polymer by reacting the PEGylated polyphosphazene intermediate with a space group selected from the group consisting of lysine ester, lysine containing oligopeptide ester, amino-ethanol, amino-propanol, amino-butanol, amino-pentanol, and amino-hexanol,
(c) connecting a linker group to the space group of the hydrophilic cationic polyphosphazene carrier polymer obtained from the step (b),
(d) connecting a drug molecules bearing OH or $NH_2$ functional group to the linker group which is connected to the hydrophilic cationic polyphosphazene carrier polymer obtained from the step (c).

Advantageous Effects

The cationic linear polyphosphazene compounds of the present invention exhibit high tumor selectivity, and the linear polyphosphazene-drug conjugate compounds of the present invention were found to be accumulated in the tumor tissues with much higher selectivity compared with that in other major organs such as liver and kidney in contrast to the conventional organic polymer-drug conjugates. Furthermore, the present linear polyphosphazene-drug conjugate compounds are stable without releasing the conjugated drug in neutral blood and organs but easily releasing in acidic tumor microenvironment, resulting in maximum drug efficacy and minimum toxicity. Thus the cationic linear polyphosphazene compounds and their anticancer drug conjugate compounds of the present invention are highly promising new materials for commercialization.

BEST MODE

Figure 1:
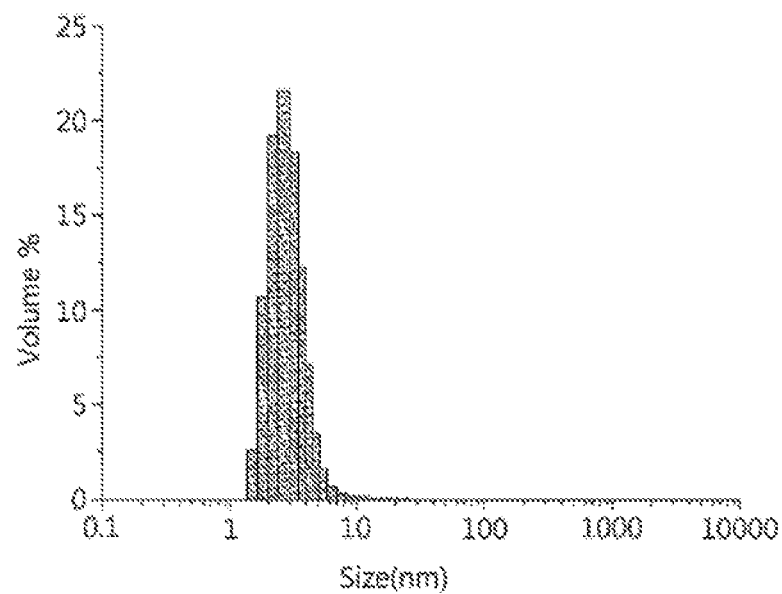
FIG. 1 shows particle size distribution of a cationic polyphosphazene compound of Example 1. (The mean diameter=3.0 nm)

The constitution and more detailed action of the present invention are provided. The present invention is embodied in the following description but is not limited thereto. The detailed constitution and action of the present invention are exemplified as in the following. In order to accomplish the afore-mentioned purpose polyphosphazene compounds represented by the following chemical formula 1 is provided.

[Chemical formula 1]

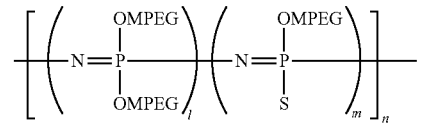

wherein n is an integer from 1 to 300; MPEG represents methoxy poly(ethylene glycol) with a molecular weight of 350 to 1000; S is a space group selected from the group consisting of lysine, arginine, glutamine, asparagine, tyrosine, lysine containing oligopeptide, arginine containing oligopeptide, glutamine containing oligopeptide, asparagine containing oligopeptide, tyrosine containing oligopeptide, amino-ethanol, amino-propanol, amino-butanol, amino-pentanol, and amino-hexanol; 1 equals to 0~0.9; m equals to 0.1~1 and 1+m equals to 1.

The above-mentioned polyphosphazene compounds of the present invention involve a hydrophilic and multifunctional lysine or lysine-containing hydrophilic oligopeptide as a side group along with the hydrophilic MPEG as another side group exhibit a lower critical solution temperature (LCST) above 100° C., which is far above the body temperature in contrast to the conventional amphiphilic polyphosphazenes showing a much lower LCST near the body temperature. Furthermore, the polyphosphazene compounds of the present invention exhibit remarkably extended blood half-life with lower systemic toxicity, and more surprising is that the polyphosphazene compounds themselves clearly show high tumor targeting properties probably due to their cationic properties and long blood circulation despite their small particle sizes (mean diameter <6 nm). The representative example of a hydrophilic oligopeptide is glycyl lysine.

The present invention also furnishes the polyphosphazene-anticancer drug conjugates represented by the following chemical formula 2.

[Chemical formula 2]

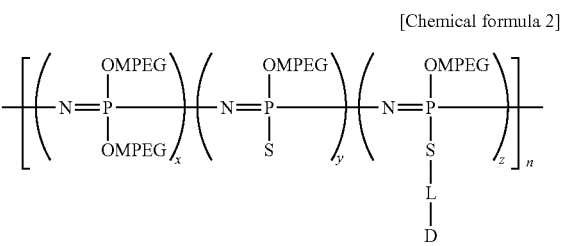

wherein n is an integer from 1 to 300; MPEG represents methoxy poly(ethylene glycol) with a molecular weight of 350 to 1000; S is a space group selected from the group consisting of lysine, arginine, glutamine, asparagine, tyrosine, lysine containing oligopeptide, arginine containing oligopeptide, glutamine containing oligopeptide, asparagine containing oligopeptide, tyrosine containing oligopeptide, amino-ethanol, amino-propanol, amino-butanol, amino-pentanol, and amino-hexanol; L is a linker to connect the spacer group of the polymer and drug molecule D bearing hydroxyl or amine group; x and y are independently in the range of 0~0.5; z is in the range of 0~1; and x+y+z=1.

For embodiment of the present invention, S represents a lysine or lysine containing dipeptide or tripeptide but is not limited thereto. For another embodiment of the present invention, S represents an amino-ethanol and amino-propanol but is not limited thereto. The drug molecule D is desired to be hydrophobic anticancer agents such as docetaxel, paclitaxel, camptothecin and (trans-(±)-1,2-diaminocyclohexane)platinum(II) but is not limited thereto. The embodiment of the present invention according to the above-mentioned chemical formula 2 may be represented by one of the following chemical formula 3 to 5.

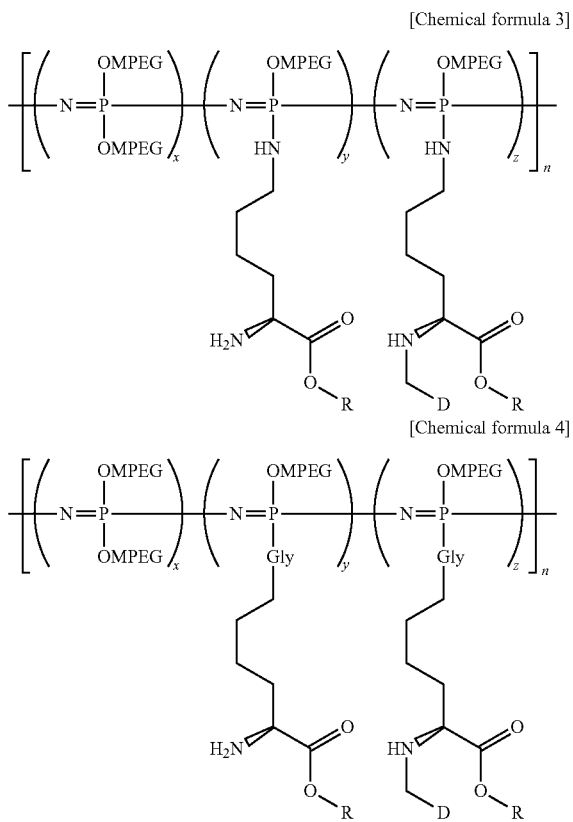

[Chemical formula 3]

[Chemical formula 4]

In chemical formula 3 and 4, n is independently an integer from 3 to 300; MPEG represents methoxy poly(ethylene glycol) with a molecular weight of 350 to 1000; D represents docetaxel, paclitaxel, camptothecin, or (trans-(±)-1,2-diaminocyclohexane)platinum(II); R is a $C_{1-6}$ linear, branched or cyclic alkyl group or $OCH_2Bz$; x and y are independently in the range of 0 to 0.5; z is larger than 0 and less than 1.0; x+y+z=1.

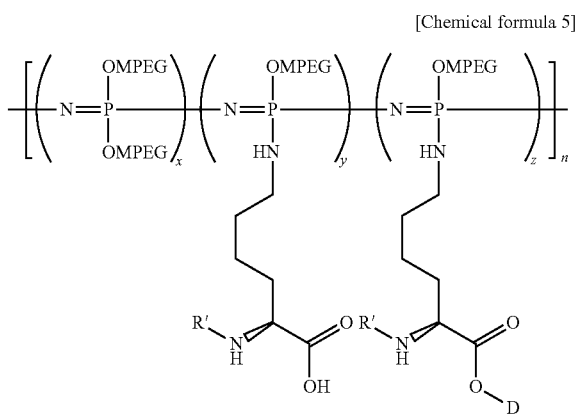

[Chemical formula 5]

Wherein n is an integer from 3 to 300; MPEG represents methoxy poly(ethylene glycol) with a molecular weight of 350 to 1000; D represents docetaxel, paclitaxel, or camptothecin; R' represents t-Boc or CBZ; x and y are independently in the range of 0 to 0.5; z is larger than 0 and less than 1.0; x+y+z=1.

The constitutional components of the present invention are explained in the following.

[Polyphosphazene Carrier Compounds]

The drug carrier polyphosphazene compounds of the present invention are a unique inorganic/organic hybrid polymer composed of inorganic polymer backbone consisting of alternating nitrogen and phosphorus atoms, grafted with two organic groups, one hydrophilic poly(ethylene glycol) for long blood circulation and another hydrophilic multifunctional lysine, lysine containing oligopeptide, or linear amino-alcohol as a space group for conjugation with hydrophobic anticancer drugs. The present inventors have discovered that the lysine group or lysine containing peptides grafted to the polyphosphazene backbone can afford cationic properties of the polyphosphazene compounds depending on the pKa value of the amino acid, which can be controlled by the amino acid employed as spacer group. The poly(ethylene glycol) employed in this invention is methoxy poly(ethylene glycol) with a molecular weight in the range of 300~2000 and its content is determined by its mole ratio to the space group determined by x, y and x depending on the required properties such as solubility, morphology and biodegradability of the final conjugate drug. The molecular weight of the polyphosphazene compounds can be controlled by the number of repeating unit n but also by the molecular weight of PEG. Compared with the branched linear organic polymers, the linear polyphosphazene compounds with two organic side groups of the present invention have higher molecular weight but smaller hydration volume, resulting in higher atomic density and better tumor selectivity.

[Anticancer Drugs]

The anticancer active drug component to be conjugated to the branched polyphosphazene compounds of the present invention should have at least one functional group of hydroxyl ($OH^-$) or amine ($NH_2$) group and more desirably be hydrophobic anticancer drugs such as taxane, camptothecin and platinum (II) drugs but is not limited thereto. In addition to these small molecular anticancer drugs any anticancer drug molecules bearing at least one hydroxyl or amine functional group can be conjugated to the present polyphosphazene carrier polymers using appropriate spacer and linker system employed in the present invention. The examples of the present invention will be demonstrated to show two kinds of anticancer drugs which exhibit lowered reactivity by steric hindrance.

The afore-mentioned polyphosphazene-taxane conjugate compounds prepared by chemical conjugation of the hydrophobic taxane drug molecules to the hydrophilic polyphosphazene carrier polymer are a new class of polymeric prodrug for intravenous injection, and their molecular weight can be controlled from 3000 to 300,000 Da, but we have discovered that the fraction of 30,000 to 100,000 Da was optimum for biocompatibility and efficacy of the conjugate drugs. The hydrophilic polyphosphazene carrier polymers of the present invention cannot form polymeric micelles in aqueous media but their conjugate chemically bound by hydrophobic taxane molecules were found to self-assemble into strong polymeric micelles with a mean diameter in the range of 20-100 nm, which exhibit outstanding tumor targeting properties by EPR effect along with long blood circulation due to the PEG outer shell of the micelles, as above-mentioned. Finally, for maximum drug efficacy along with minimum systemic toxicity of the polyphosphazene-taxane conjugate, an acid (pH=4~7) cleavable linker, aconitic anhydride was employed to link the anticancer drug component taxane molecules to the carrier polyphosphazene so that the strongly cytotoxic taxane drug molecules are not significantly released from the polyphosphazene-taxane conjugate during their circulation in the neutral blood system (pH=7.2) but easily released at the tumor site which is in the acidic tumor microenvironment.

The docetaxel drug molecule, as displayed in the following chemical formula 6, has four hydroxyl groups at 2, 7, 10, and 2' positions, but 2' hydroxyl group is known to be most active, and therefore, the drug molecule was linked to the carboxylic acid group of the linker aconitic anhydride by esterification to make a precursor, which is then reacted to form an amide bond with the amine group of the spacer group amino acid or amino-ethanol of the polyphosphazene carrier polymer. In case of paclitaxel the same reaction scheme may be applied. It should be pointed out here two important reasons for employment of a multifunctional aconitic anhydride as a linker for conjugation of taxane drug molecules to the polyphosphazene compounds of the present invention. It is well known that when sterically hindered drug molecules are introduced for conjugation to the polymeric drug carriers by esterification, the product yield is not only very low but also sterically different isomers may be resulted. It was found from the preliminary study that when docetaxel was directly introduced to the aconitic anhydride linked to the polyphosphazene carrier polymers not only long reaction time over 24 hours were required but also a few sterically different isomers were resulted. However, the present inventors have discovered that when docetaxel was reacted first with the linker aconitic anhydride to prepare a precursor, which was reacted with the polyphosphazene carrier polymers of the present invention, both high product yield and purity of the final polyphosphazene-docetaxel conjugate could be accomplished.

[Chemical formula 6]

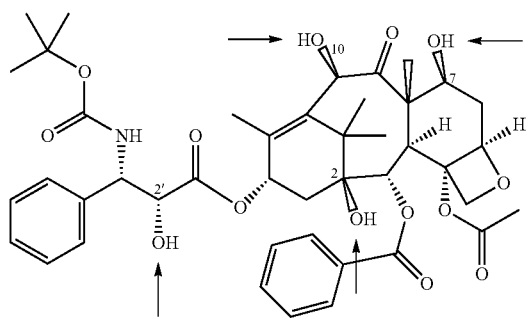

The present invention involves camptothecin series of the following exemplified compounds but is not limited thereto, including all the pharmaceutically active derivatives, particularly irinotecan, topotecan, and belotecan.

[Spacer (S)]

In the present invention a multifunctional space group is introduced to the polyphosphazene carrier polymer to chemically connect them to the linker aconitic anhydride for conjugation with anticancer drugs. The spacer group should contain a primary amine group to connect to the above-mentioned linker group and another primary amine or alcoholic group for grafting to the polyphosphazene backbone and is one selected from the multifunctional amino acid groups of lysine, arginine, glutamine, asparagine, tyrosine, and these amino acid containing oligopeptides or linear amino-alcohols. The afore-mentioned amino acids are classified as basic amino acids, and when such a basic amino acid is introduced to the polyphosphazene backbone, cationic properties can be afforded to the polyphosphazene compounds in a specific pH range depending on its pKa value of the amino acid. The space group may be not only a single amino acid but also a combination of more than two amino acids. For example, glycyl lysine (Gly-Lys), alanyl lysine (Ala-Lys), or a tripeptide may be employed. Furthermore, for a certain multifunctional amino acid or peptide, the carboxylic ester group may be hydrolyzed for direct conjugation with drug molecules without linker. Such a representative example is lysine, which will be illustrated in Examples.

[Linker]

The drug efficacy of the polymeric drug conjugates is well known to be critically dependent on the releasing kinetics of the active drug molecules from the polymeric carrier. In the present invention the active drug molecules were conjugated to the polyphosphazene carrier polymers by either amide bonding (—CONH—) or ester boding (—COO—) by appropriate selections of the space group and the linker aconitic anhydride depending on the molecular structures of drug and carrier systems, which is different from the conventional method useful only for the drug molecules bearing a primary amine group. Thus the present invention furnishes a new and upgraded spacer-linker system for introduction of acid-cleavable linker for drug conjugation.

The afore-mentioned conjugation reactions may be performed under general coupling reaction conditions in any organic solvents inert to the conjugation reactions including dichloromethane, chloroform, acetonitrile, 1,4-dioxane, dimethyl formamide, and tetrahyrofuran. However, because of instability of the reaction intermediates to be formed during introduction of the linker, the whole reactions were performed in dried solvents and under dried argon atmosphere at low temperature (−10~0° C.) to increase reaction efficiency. In particular, cis-aconitic anhydride linker is known to undergo its anhydride ring opening reaction in basic solution, resulting in isomers, and therefore, instead of the basic catalyst DMAP (dimethylaminopyridine), DPTS (dimethylaminopyridine/p-toluene sulfonic acid) was employed as a catalyst to perform the reaction in neutral state. The representative drugs appropriate for preparation of the polyphosphazene conjugate compounds are oligopeptides, polypeptides, monomeric drugs, antibody, nucleotides, lipids, and any other materials bearing —OH or $NH_2$ functional group.

The linkers usable in the present invention are listed in the following chemical formula 7 to 11 but chemical formula 7 is most preferred.

[Chemical formula 7]

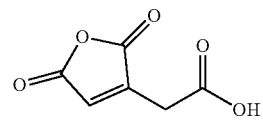

[Chemical formula 8]

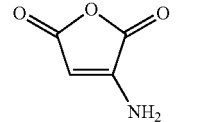

[Chemical formula 9]

[Chemical formula 10]

[Chemical formula 11]

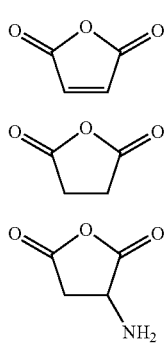

In case of acid cleavable (pH=5.5) aconitic anhydride of the above chemical formula 7 employed as a linker the polymer conjugate drugs may be prepared according to the following reaction scheme 1.

In contrast to the above reaction schemes 1 and 2 starting from the anhydride ring opening reaction of the aconitic anhydride, the following reaction scheme 3 discovered in the present invention shows that instead of the aconitic anhydride ring opening reaction its carboxylic group was reacted with the hydroxyl group of a drug molecule (HOR') to form an ester bond yielding a drug precursor. This precursor was then conjugated to the drug carrier polymer (RNH$_2$) by the anhydride ring opening reaction using the spacer amine group of the carrier polymer. The aconitic anhydride ring opening reaction also can be performed using excess NHS(N-hydroxy succinimide) as shown in the above reaction scheme. This synthetic route gives important advantages over the afore-mentioned methods. First of all, inactive isomers shown in the above Reaction schemes 1 and 2 can be avoided, resulting in much higher yield of the final conjugate drug, and the purity of the conjugate drug as well as drug efficacy could be reasonably controlled.

[Reaction scheme 1]

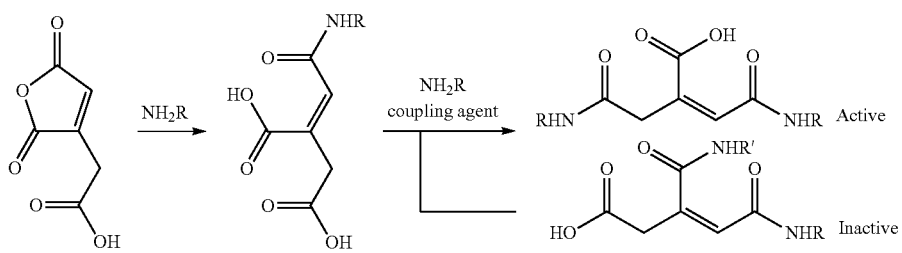

However, in this reaction scheme an inactive isomer unable to release the drug moiety is formed, and depending on the conjugation site, drug releasing rate and drug efficacy is difficult to control. In particular, in case of both the spacer/linker and linker/drug bonds are amide bond, an isomer (Reaction scheme 1 Inactive) difficult to release drug molecules by hydrolysis may be formed, resulting in low drug efficacy. In case of Reaction scheme 2 showing both spacer/linker and linker/drug bonds are ester bond, also inactive form may be resulted although hydrolysis by enzymes may be workable. Also, in case of the anhydride ring opening by using the OH group of drug molecule, nucleophilic agent should be used in large excess particularly for sterically hindered drug. In case of taxane drugs of the present invention approximately 20 times excess amount was required to complete the reaction. In such case, the product yield of the final polyphosphazene-drug conjugate was found to be less than 5%, which is not commercially feasible.

[Reaction scheme 2]

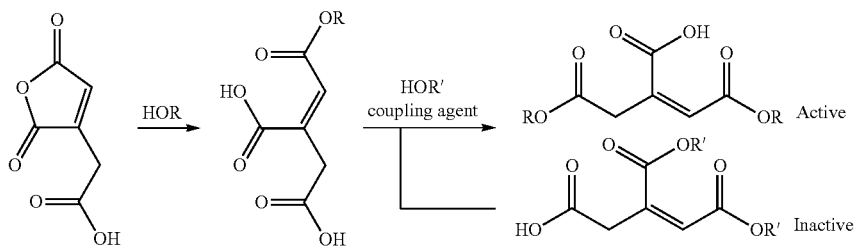

[Reaction scheme 3]

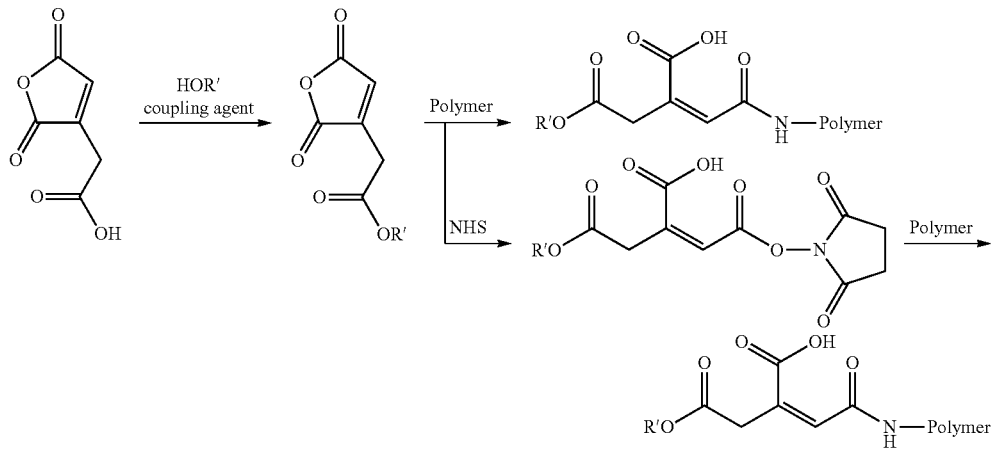

The present invention also provides detailed synthetic methods of the linear polyphosphazene compounds and polyphosphazene-drug conjugate compounds. In this regard, the concrete examples of the drug, spacer and linker groups will be demonstrated, but the present invention is not limited to such examples.

The linear polyphosphazene compounds of the present invention is synthesized by grafting a hydrophilic poly (ethylene glycol) (PEG) and a multifunctional lysine bearing two primary amine and one carboxyl groups, lysine containing oligopeptides or amino-ethanol to the dichlorophosphazene backbone (—N=PCl$_2$—). The multifunctional lysine, lysine containing oligopeptides or linear amino-alcohol of thus prepared polyphosphazene compounds may be used as a space group to conjugate with hydrophobic anticancer drugs such as taxane, platinum(II) complex or camptothecin using a linker such as aconitic anhydride to produce novel acid cleavable linear polyphosphazene-drug conjugates.

The linear polyphosphazene-drug conjugate compounds of the present invention exhibited outstanding tumor selectivity by selective accumulation in tumor tissue, and it was found that by controlling the x, y, and z value of the afore-mentioned chemical formula 2 highly water soluble, long blood circulating and excellent tumor targeting anticancer drugs could be prepared.

In the present invention the spacer group selected from the afore-mentioned lysine, arginine, glutamine, asparagine, or tyrosine containing oligopeptides is desirably lysine and glycine containing oligopeptide, for example, dipeptide and tripeptide and more desirably glycyllysine but is not limited thereto. In the afore-mentioned oligopeptides lysine is desired to be located at the terminal position to conjugate with taxane anticancer drug. The space group selected from the linear amino-alcohols is desirably amino-ethanol, amino-propanol, amino-butanol, amino-pentanol and amino-heanol, and more desirably amino-ethanol and amino-propanol.

In the present invention the taxane anticancer drug (D) molecules are conjugated to the polyphosphazene carrier polymer through the lysine amine or carboxyl group, and in case the carboxyl group is used for conjugation, the amine group should be blocked by a blocking group such as t-Boc, FMOC, or CBZ. In the afore-mentioned chemical formula 2, L is a linker to connect the anticancer drug (D) and spacer group of the carrier polymer (S) and is cis-aconitic anhydride, succinyl anhydride, or maleic anhydride and desirably cis-aconitic anhydride. The anticancer drug components (D) exemplified in the present invention are taxane family, camptothecin family, and platinum complexes including docetaxel, paclitaxel, camptothecin, topotecan, irinotecan, belotecan, oxaliplatin, but is not limited to these drugs.

The polyphosphazene-drug conjugates of the present invention have a narrow molecular weight distribution in the range of 3,000-300,000 and desirably in the range of 30,000-100,000 and are highly soluble in water by self-assembling into polymeric micelles with a mean diameter in the range of 20~200 nm depending on the hydrophobicity of the drug molecules (D). As above-mentioned, such polymeric micelles assembled from the polyphosphazene-drug conjugates of the present invention exhibit excellent tumor selectivity attributed to their EPR effect.

The polyphosphazene and polyphosphazene-taxane conjugate compounds can be prepared by the following four step synthetic reactions.

(a) The starting material hexachlorocyclotriphosphazene is converted by thermal polymerization into linear poly(dichlorophosphazene), (N=PCl$_2$)$_n$, which is then reacted with sodium salt of poly(ethylene glycol) to obtain an intermediate polyphosphazene, [N=PCl (MPEG)]n;

(b) The above polyphosphazene intermediate is reacted with one selected from the group consisting of lysine ester, lysine containing oligopeptide, amino-ethanol, amino-propanol, amino-butanol, amino-penanol, and amino-hexanol to prepare hydrophilic cationic polyphsphazene carrier polymers;

(c) An anticancer drug bearing hydroxyl (OH) or primary amine (NH$_2$) group is reacted with a linker group, for example, aconitic anhydride, to prepare a precursor; and (d) Finally, the precursor of step (c) is reacted with the polyphsphazene carrier polymer of step (b) to obtain the final polyphosphazene conjugate compound of chemical formula 2.

[Chemical formula 2]

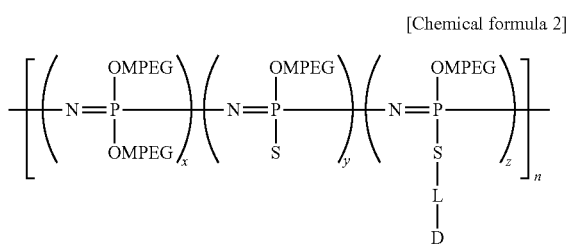

wherein n is an integer from 1 to 300; MPEG represents methyl poly(ethylene glycol) with a molecular weight of 350 to 1000; S is a space group selected from the group consisting of lysine, arginine, glutamine, asparagine, tyrosine, lysine containing oligopeptide, arginine containing oligopeptide, glutamine containing oligopeptide, asparagine containing oligopeptide, tyrosine containing oligopeptide, amino-ethanol, amino-propanol, amino-butanol, amino-pentanol, and amino-hexanol; L is a linker to connect the spacer group of the polymer and drug molecule D bearing hydroxyl or amine group; x and y are independently in the range of 0~0.5; z is in the range of 0~1; and x+y+z=1.

In another embodiment of the present invention, the anticancer drug bearing hydroxyl (OH) or primary amine ($NH_2$) group can be one selected from the group of docetaxel, paclitaxel, camptothecin, and (trans-(±)-1,2-diaminocyclohexane)platinum(II), but is not limited to these drugs.

Furthermore, the abovementioned four stepwise reactions to prepare polyphosphazene-drug conjugates may be subjected to a little modification depending on the structure of drug molecules to be conjugated. For example, in case of platinum(II) complex, instead of preparation of the precursor by reaction of a drug with the linker at step (c) followed by reaction of the precursor to the polymer carrier at step (d), the linker group is reacted to the polymer carrier at step (c), and then drug is linked to the linker group connected to the carrier polymer at step (D).

All the following synthetic reaction procedures should be performed under carefully controlled inert atmosphere using dried argon or nitrogen and thoroughly dried solvents. Detailed synthetic procedures are described in the following.

Step (a)

Hexachlorocyclotriphosphazene, $(N=PCl_2)_3$, shown in chemical formula 12 was subjected to thermal polymerization according to the literature procedure (Youn Soo Sohn, et al. *Macromolecules*, 1995, 28, 7566) to obtain poly(dichlorophosphazene) $(N=PCl_2)_n$ with an average molecular weight of $10^4$~$10^5$ as represented in chemical formula 13.

[Chemical formula 12]

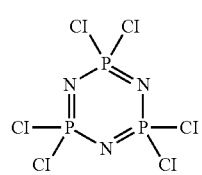

[Chemical formula 13]

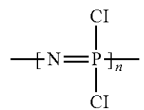

Wherein n represents the degree of polymerization in the range of 3 to 300.

The monomethoxy poly(ethylene glycol) of chemical formula 14 was dried by using azeotropic mixture of toluene and water and then reacted with sodium metal to convert to sodium salt of chemical formula 15, which was then reacted with poly(dichlorophosphazene) of chemical formula 13 in the presence of triethylamine to complete PEGylation of polyphosphazene of chemical formula 15.

[Chemical formula 14]

[Chemical formula 15]

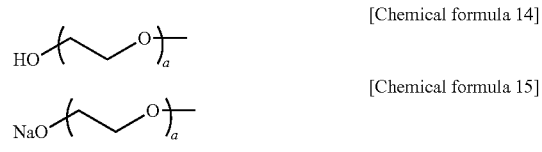

In the above chemical formula 14 and 15 a is the degree of polymerization of PEG and is 7 to 22.

More detailed procedure for preparation of PEGylated polyphosphazene is described in the following.

The hexachlorocyclotriphosphazene $(N=PCl_2)_3$ of chemical formula 12 and 3 to 10% anhydrous aluminum chloride are mixed homogeneously in the glove box and then sealed in a Pyrex ample under vacuum. The ample was heated to 230-250° C. with rotation in a heating chamber for 3-5 h to obtain a clear viscous liquid of poly(dichlorophosphazene). In the meantime, monomethoxy poly(ethylene glycol) of chemical formula 14 is reacted with 1.2-1.5 equivalent sodium metal in an unreactive anhydrous organic solvent such as tetrahydrofuran (THF), benzene and toluene to obtain a sodium salt of chemical formula 15. To a solution of one molar poly(dichlorophosphazene) of chemical formula 13 dissolved in the same solvent was added 0.5-1.8 equivalent of the sodium salt of chemical formula 15 above prepared. The reaction solvent may be any unreactive solvent but desirably tetrahydrofuran, benzene, toluene and chloroform. The sodium salt solution of chemical formula 15 should be added slowly for 2-8 h to the poly(dichlorophosphazene) solution cooled to below 0° C., and then the reaction mixture was further reacted at ambient temperature for 6-24 h to obtain the PEGylated polyphosphazene intermediate of chemical formula 16.

[Chemical formula 16]

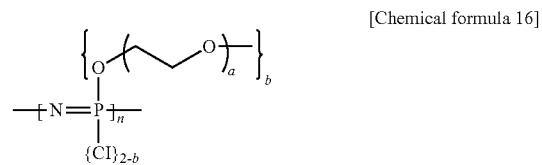

Wherein n is the degree of polymerization of polyphosphazene in the range of 3 to 300, a is the degree of polymerization of methoxy poly(ethylene glycol) in the range of 7 to 22, and b is the substituted mole fraction of methoxy poly(ethylene glycol) in the range of 0.5 to 1.8.

Step (b)

In order to substitute the rest (2-b) chlorine atoms of the PEGylated polyphosphazene of chemical formula 16 with a space group for drug conjugation, 1.5-1.8 equivalent of lysine ester or lysine containing oligopeptide ester dissolved along with 6 equivalent triethylamine in any unreactive organic solvent, desirably, tetrahydrofuran, chloroform, or dichloromethane is slowly added to the above PEGylated polyphosphazene intermediate solution of chemical formula 16 and then refluxed at 40-60° C. for 12 h to 3 days. As a lysine ester the lysine derivatives of chemical formula 17 may be used and as a lysine containing oligopeptide ester the derivatives of chemical formula 18 may be used. In the chemical formula glycine may be substituted by leucine, isoleucine, phenyl alanine, and valine.

[Chemical formula 17]

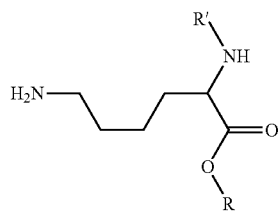

Wherein R is linear, branched, or cyclic $C_{1-6}$ alkyl group, or $OCH_2Bz$, and R' is amine protecting group, t-Boc (tert-butoxycarbonyl), Fmoc (fluorenylmethyloxycarbonyl) or CBZ (carbozenyloxy).

[Chemical formula 18]

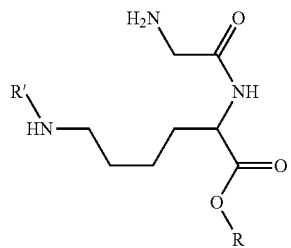

Wherein R is a linear, branched, or cyclic $C_{1-6}$ alkyl group, or $OCH_2Bz$, and R' is an amine protecting group, t-Boc (tert-butoxycarbonyl), Fmoc (fluorenylmethyloxycarbonyl) or CBZ (carbozenyloxy).

In the present invention, R may be methyl, ethyl, n-propyl, n-butyl or t-butyl, but is not limited to them.

The above-mentioned reaction solution was centrifuged or filtered to remove the byproduct precipitate ($Et_3NHCl$ or NaCl) and the filtrate was subjected to concentration. Ethanol was added to the concentrate followed by vacuum concentration to remove organic solvents completely. The oily product was dissolved in a small amount of ethanol (100 ml) and then a large amount of water (900 ml) was added for recrystallization at low temperature, and then subjected to membrane ultrafiltration using membranes with different pore sizes to fractionate the polymers into molecular weight of 50,000 to 100,000. The fractionated polyphosphazene solution was subjected to freeze-dry to obtain polyphosphazene compounds of chemical formula 19 and chemical formula 20 in approximately 40-50% yield.

[Chemical formula 19]

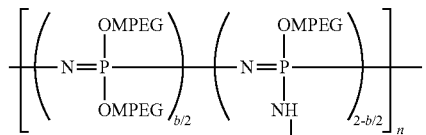

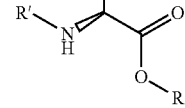

[Chemical formula 20]

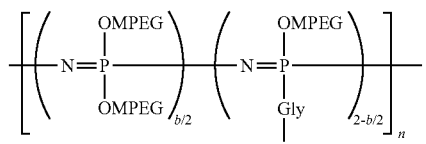

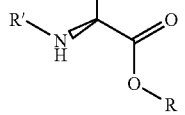

In chemical formula 19 and 20, n is the degree of polymerization of polyphosphazenes ranging in 3 to 300; MPEG represents methoxy poly(ethylene glycol) with a molecular weight of 350 to 1000; b has a value of 0.5-1.8; R is a linear, branched, or cyclic $C_{1-6}$ alkyl group, or $OCH_2Bz$; and R' is an amine protecting group, t-Boc (tert-butoxycarbonyl), Fmoc (fluorenylmethyloxycarbonyl) or CBZ (carbozenyloxy).

Step (c)

It is not difficult to conjugate a drug molecule with a functional group to the polyphosphazene compounds bearing a multifunctional space group prepared at Step (b), but it is not easy to conjugate a drug molecule bearing multifunctional groups such as taxane to the multifunctional polyphosphazene carrier polymer in a desired bonding mode which is clinically useful. In other words, the anticancer drug-polyphosphazene conjugate is required to exhibit strong tumor targeting properties and drug releasing kinetics in addition to satisfactory physicochemical properties. In particular, the drug releasing kinetics of the polymer conjugate is known to be critically important for drug efficacy, and therefore, the role of linker of the present invention is very important. In more concrete, the linker group should not only be able to connect easily the functional group of drug molecule (OH, $NH_2$) to the functional groups of the polyphosphazene carrier polymer (COOH, $NH_2$), but also be able to let the conjugate drug to release easily drug molecules in the targeted tumor site.

It has been discovered in the present invention that cis-aconitic anhydride of chemical formula 7 is the best linker for conjugation of taxane to the polyphosphazene carrier polymer in both aspects of synthetic and drug releasing kinetics, particularly when the linker is reacted first with taxane to prepare a precursor, which is then linked to the space group of polyphosphazenes. The taxane drug precursor is prepared as in the following.

Docetaxel (1.0 mmol, 803 mg) and cis-aconitic acid anhydride (2.0 mmol, 312 mg) are mixed under argon atmosphere and dissolved in THF or dichloromethane. The mixed solution is cooled to the freezing point and then DIC (N,N'-diisopropylcarbodiimide) (2.0 mmol, 0.252 g) and DPTS (4-(N,N'-dimethylamino)pyridinium-4-toluene sulfonate) (2.0 mmol, 0.58 g) are added to perform esterification reaction between carboxylic acid group of the linker aconitic acid and 2'-hydroxy group of docetaxel for 12 h. After confirming the completion of the reaction by TLC, excess amounts of NHS (N-hydroxy succinimide) and DIPEA (diisopropylethylamine) are added to open the anhydride ring of aconitic acid unreacted. The aconitic anhydride ring is known to be easily opened by hydroxyl and amine group in basic solution. After stirring for 12 h the reaction mixture is cooled to 0° C. for 3 h, and then vacuum filtered to remove precipitate. The filtrate is subjected to vacuum distillation to remove all the organic solvents to obtain an oily mixture, which is dissolved in ethanol (50 ml). A large excess amount of water (500 ml) is added to this ethanol solution for recrystallization for 3 h in refrigerator. The supernatant liquid is removed to obtain an oily product which is completely dissolved in 300 ml dichloromethane. This dichloromethane solution is washed with saturated salt solution three times and then the collected organic layer is dried using anhydrous $NaHCO_3$ and then subjected to vacuum evaporation to obtain the precursor in 95% yield.

Step (d)

To the afore-mentioned polyphospazene carrier polymer prepared at step (b) a hydrophobic anticancer drug such as taxane is conjugated to obtain a novel polyphosphazene-taxane conjugate represented by chemical formula 2. There are two different ways to conjugate taxane molecules to the polyphosphazene carrier polymer: one is that the taxane molecule is linked via aconitic acid to the lysine amine of the polyphosphazene carrier by amide bonding and another is esterification of the lysine carboxyl group of the polyphosphazene carrier with 2'-hydroxyl group of the taxane molecule. Therefore, the step (d) is performed in two different methods.

In the amide bonding method, the protecting group (t-Boc) of the afore-mentioned polyphosphazene carrier polymer of chemical formula 19 or chemical formula 20 should be removed by reaction with a mixture of trifluoroacetic acid and methylene chloride (2:1) for 6 h followed by neutralization, washing with water and then freeze-drying. Such an unblocked polyphosphazene carrier polymer is reacted for 12 h with a drug precursor, aconitic taxane-NHS (N-hydroxysuccinimidyl) prepared by reaction of the linker aconitic anhydride with the drug such as taxane followed by addition of excess NHS (N-hydroxysuccinimide) and DIPEA (diisopropylethylamine). The resultant reaction mixture is subjected to vacuum evaporation for concentration for 12 h and then dissolved in ethanol. The final solution is subjected vacuum evaporation (37° C., 5 mm bar) to remove all the trace of solvents and DIPEA. The residual polymer conjugate product is dissolved in 50 ml of ethanol and then 950 ml of distilled water is added to the ethanol solution for recrystallization in refrigerator. After 3 h the solution mixture is vacuum filtered to collect the final polymer conjugate product, which is washed several times with 30% ethanol solution and then distilled water using ultra-membrane until less than 0.1% unreacted taxane is detected by UV spectroscopy. The purified polyphosphazene-taxane conjugate solution is freeze dried to obtain the final product of chemical formula 3 or 4.

In the ester bonding method, the terminal lysine ester of the spacer group of polyphosphazene carrier polymer can be hydrolyzed to carboxylic acid form using an alkali and then esterification with the 2'-hydroxyl group of taxane can be performed. For example, the polyphosphazene carrier polymer of chemical formula 19 is dissolved in methanol and then excess amount of KOH or NaOH (150~200%) is added thereto to obtain the potassium or sodium salt of lysine of the carrier polymer. The methanol solvent is removed by vacuum evaporation and the resultant metal salt is dissolved in distilled water (100 ml). Methylene chloride or chloroform (300 ml) is added to this solution, which is acidified by slow addition of an organic acid. When the pH of the water layer is lowered down to 4-3, the polyphosphazene carrier polymer in acidic form is extracted into the organic layer by shaking the two solvent layers. Such extraction procedure is repeated three times and the collected organic layer solution is dried by anhydrous sodium bicarbonate. Filtration and vacuum evaporation of the dried solution gives a polyphosphazene carrier polymer bearing terminal hydrolyzed lysine group. The resulting polyphosphazene carrier polymer bearing hydrolyzed lysine and equivalent docetaxel are dissolved in tetrahydrofuran and then N,N'dicyclohexylcarbodiimide and triethylamine are added thereto for esterification reaction. Completion of the reaction is confirmed by TLC using a solvent mixture ($CHCl_3$:$MeOH_3$=10:1), and then the reaction mixture is subjected to vacuum distillation to concentrate the reaction mixture, followed by ultra-membrane fractionation of the molecular weight of 30 to 100 kDa of the final polyphosphazene-docetaxel conjugate of chemical formula 5.

Hereinafter the constitution and action of the present invention will be described in more detail with reference to the following examples and demonstrations, but the present invention is not limited thereto. In the following examples, elemental analysis of carbon, hydrogen and nitrogen for the compounds of the present invention was performed using Perkin-Elmer C, H and N analyzer. Hydrogen and nitrogen nuclear magnetic resonance spectra were measured using Varian Gemini-500 NMR Spectrometer. The particle size distributions of polyphosphazene carrier polymers and their drug conjugates were measured using Malvern Zeta-sizer (Nano-ZS).

MODE FOR INVENTION

Synthesis of Polyphosphazene Compounds (Drug Delivery Systems)

EXAMPLE 1

Synthesis of $[NP(MPEG550)_{1.5}(LysEt)_{0.5}]_n$

Hexachlorocyclotriphosphazene ($[NPCl_2]_3$, 11.54 g, 100 mmol) and anhydrous aluminum chloride ($AlCl_3$, 7.5 wt %) are mixed homogeneously in glove box and then subjected to thermal polymerization at 250° C. for 5 h according to the literature procedure (Sohn Y. S. et al. *Macromolecules* 1995, 28, 7566) to obtain poly(dichlorophosphazene) ($[NPCl_2]_n$). In the meantime, methoxypoly(ethylene glycol) with an average molecular weight of 550 (MPEG550) (82.5 g, 150 mmol) is reacted with sodium metal (4.9 g, 200.4 mmol) at 120° C. for 6 h in dried toluene solvent under argon atmosphere to obtain sodium salt of MPEG550. To the above poly(dichlorophosphazene) dissolved in tetrahydrofuran (100 ml) in a glass vessel is added slowly for 60 min the solution of sodium salt of MPEG550 prepared in ice bath (0° C.). After 1 h the ice bath is removed and then the reaction mixture is subjected to further reaction at ambient temperature for 12 h to obtain PEGylated polyphosphazene intermediate solution. In a separate vessel Boc-lysine ethyl ester (N-Boc-LysEt, 20.5 g, 75.0 mmol) neutralized by dried trimethylamine in dried chloroform (200 ml) is slowly added to the above PEGylated polyphosphazene intermediate solution and the reaction mixture is further reacted at room temperature for 24 h. The reaction mixture is filtered to remove the resultant byproduct precipitates ($NEt_3 \cdot HCl$ or NaCl) and the filtrate is subjected to vacuum evaporation to concentrate the solution, which is dissolved in ethanol followed by vacuum evaporation. Finally the residue is dissolved in distilled water, which is filtered to remove any insoluble, and the filtrate is subjected to dialysis using ultra membrane (CE, MWCO=3000) to remove lower molecular weight fraction under 3000 Da. The fractionated polypphosphazene polymer is washed with distilled water more than 5 times and then freeze-dried. The resultant polypphosphazene polymer is dissolved in a dichloromethane solution (200 ml) containing 30% (v/v) trifluoroacetic acid, which is stirred for 6 h to remove the blocking group (t-Boc) from the polymer to obtain the unblocked polypphosphazene polymer $[NP(MPEG550)_{1.5}(LysEt)_{0.5}]_n$ in 65% yield (3.37 g). After confirming the unblocked lysine amine by proton NMR, the polymer solution was neutralized by tri-ethyl amine, followed by vacuum distillation to remove organic solvent. To the resulting polymer aqueous sodium bicarbonate solution was added to dissolve the polymer completely, which was desalted and then fractionated using ultra-membranes with molecular weight cut-off at 3k Da, 30 k Da, 100 k Da. The overall recovery yield was 90%.

Composition: $C_{83}H_{170}N_4O_{41}P_2$.

Elemental analysis data (%): C, (51.66); H, (8.59); N, (2.83). Theoretical value: (51.33); H, (8.82); N, (2.88).

$^1$H-NMR spectra ($CDCl_3$) (δ, ppm): 1.25 (s, 1.5H, Lys-$OCH_2CH_3$), 2.49 (br, 1.00H, suucinyl-$CH_2$), 2.90 (br, 1.00H, Lys-ε-$CH_2$), 3.38 (s, 4.50H, MPEG550-$OCH_3$), 3.65 (br, 66.0H, MPEG550-$OCH_2CH_2$), 4.4 (s, 1H, Lysine-CH.

$^{31}$P-NMR spectra: ($CDCl_3$, ppm): δ −0.014 (s), δ −5.551 (s).

EXAMPLE 2

Synthesis of $[NP(MPEG750)_{1.5}(LysEt)_{0.5}]_n$

According to the same procedure as described in Example 1, the desired product of the title polyphosphazene compound was prepared using hexachlorocyclotriphosphazene ($[NPCl_2]_3$, 11.54 g, 100 mmol), methoxypoly(ethylene glycol) with an average molecular weight of 750 (MPEG750, 112.5 g, 150 mmol), trimethylamine (80.0 ml, 600 mmol), and Boc-LysEt, (20.5 g, 75 mmol) in 74% yield.

Composition: $C_{107}H_{218}N_4O_{53}P_2$.

Elemental analysis data (%): C, (51.30); H, (8.99); N, (2.36). Theoretical value: (52.01); H, (8.89); N, (2.27).

$^1$H-NMR spectra ($CDCl_3$) (δ, ppm): 1.25 (s, 1.50H, Lys-$OCH_2CH_3$), 1.39-1.98 (br, 3.00H, Lys-$CH_2$), 2.90 (br, 1H, Lys-ε-$CH_2$), 3.38 (s, 4.50H, MPEG750-$OCH_3$), 3.65 (br, 98.0H, MPEG750-$OCH_2CH_2$), 4.01 (bs, 6H, MPEG750-$CH_2$), 4.45 (m, 0.5H, Lys-CH).

$^{31}$P-NMR spectra: ($CDCl_3$, ppm): δ −0.014 (s), δ −5.551 (s).

EXAMPLE 3

Synthesis of $[NP(MPEG1000)_{1.5}(LysEt)_{0.5}]_n$

According to the same procedure as described in Example 1, the desired product of the title polyphosphazene compound was prepared using hexachlorocyclotriphosphazene ($[NPCl_2]_3$, 11.54 g, 100 mmol), methoxypoly(ethylene glycol) with an average molecular weight of 1000 (MPEG1000, 150 g, 150 mmol), trimethylamine (80.0 ml, 600 mmol), and Boc-LysEt, (20.5 g, 75 mmol) in 74% yield.

Composition: $C_{143}H_{290}N_4O_{71}P_2$.

Elemental analysis data (%): C, (53.01); H, (8.70); N, (2.36). Theoretical value: (52.62); H, (8.96); N, (1.72).

$^1$H-NMR spectra ($CDCl_3$) (δ, ppm): 1.25 (s, 1.50H, Lys-$OCH_2CH_3$), 1.39-1.98 (br, 3.00H, Lys-$CH_2$), 2.90 (br, 1H, Lys-ε-$CH_2$), 3.38 (s, 4.50H, MPEG1000-$OCH_3$), 3.65 (br, 130.0H, MPEG1000-$OCH_2CH_2$), 4.45 (m, 0.5H, Lys-CH).

$^{31}$P-NMR spectra: ($CDCl_3$, ppm): δ −0.014 (s), δ −5.551 (s).

EXAMPLE 4

Synthesis of $[NP(MPEG550)_{1.25}(LysEt)_{0.75}]_n$

According to the same procedure as described in Example 1, the desired product of the title polyphosphazene compound was prepared using hexachlorocyclotriphosphazene ($[NPCl_2]_3$, 11.54 g, 100 mmol), methoxypoly(ethylene glycol) with an average molecular weight of 550 (MPEG550, 69.0 g, 126 mmol), trimethylamine (80.0 ml, 600 mmol), and Boc-LysEt, (27.4 g, 100 mmol) in 74% yield.

Composition: $C_{74.5}H_{153}N_5O_{35.5}P_2$

Elemental analysis data (%): C, (50.87); H, (9.02); N, (4.31). Theoretical value: (51.14); H, (8.82); N, (4.14).

$^1$H-NMR spectra ($CDCl_3$) (δ, ppm): 1.25 (s, 2.25H, Lys-$OCH_2CH_3$), 1.39-1.98 (br, 4.50H, Lys-$CH_2$), 2.90 (br, 1.5H, Lys-ε-$CH_2$), 3.38 (s, 3.75H, MPEG550-$OCH_3$), 3.65 (br, 82.5H, MPEG550-$OCH_2CH_2$), 4.45 (m, 0.7H, Lys-CH).

$^{31}$P-NMR spectra: ($CDCl_3$, ppm): δ −0.014 (s), δ −5.551 (s).

EXAMPLE 5

Synthesis of $[NP(MPEG550)_{1.0}(LysEt)_{1.0}]_n$

According to the same procedure as described in Example 1, the desired product of the title polyphosphazene compound was prepared using hexachlorocyclotriphosphazene ($[NPCl_2]_3$, 11.54 g, 100 mmol), methoxypoly(ethylene glycol) with an average molecular weight of 550 (MPEG550, 55.0 g, 100 mmol), trimethylamine (80.0 ml, 600 mmol), and Boc-LysEt, (35.6 g, 130 mmol) in 74% yield.

Composition: $C_{66}H_{136}N_6O_{30}P_2$

Elemental analysis data (%): C, (50.29); H, (8.95); N, (5.51). Theoretical value: (50.95); H, (8.81); N, (5.40).

$^1$H-NMR spectra ($CDCl_3$) (δ, ppm): 1.25 (s, 3.00H, Lys-$OCH_2CH_3$), 1.39-1.98 (br, 6.00H, Lys-$CH_2$), 2.90 (br, 2.0H, Lys-ε-$CH_2$), 3.38 (s, 3.0H, MPEG550-$OCH_3$), 3.65 (br, 66.0H, MPEG550-$OCH_2CH_2$), 4.45 (m, 1.0H, Lys-CH).

$^{31}$P-NMR spectra: ($CDCl_3$, ppm): δ −0.014 (s), δ −5.551 (s).

EXAMPLE 6

Synthesis of [NP(MPEG550)$_{1.5}$(GlyLysEt)$_{0.5}$]$_n$

According to the same procedure as described in Example 1, the desired product of the title polyphosphazene compound was prepared using hexachlorocyclotriphosphazene ([NPCl$_2$]$_3$, 11.54 g, 100 mmol), methoxypoly(ethylene glycol) with an average molecular weight of 550 (MPEG550, 82.5 g, 150 mmol), trimethylamine (80.0 ml, 600 mmol), and Gly(N$^\varepsilon$—BocLysEt (24.8 g, 90 mmol) in 74% yield.

Composition: C$_{85}$H$_{173}$N$_5$O$_{42}$P$_2$
Elemental analysis data (%): C, (50.75); H, (8.82); N, (3.61). Theoretical value: (51.06); H, (8.72); N, (3.50).
$^1$H-NMR spectra (CDCl$_3$) (δ, ppm): 1.25 (s, 3.00H, Lys-OCH$_2$CH$_3$), 1.39-1.98 (br, 6.00H, Lys-CH$_2$), 2.90 (br, 2.0H, Lys-ε-CH$_2$), 3.38 (s, 3.0H, MPEG750-OCH$_3$), 3.65 (br, 66.0H, MPEG500-OCH$_2$CH$_2$), 3.92 (bs, 2H, Gly-CH$_2$), 4.45 (m, 1.0H, Lys-CH).
$^{31}$P-NMR spectra: (CDCl$_3$, ppm): δ −0.014 (s), δ −5.551 (s).

EXAMPLE 7

Synthesis of [NP(MPEG550)$_{1.5}$(N$^\alpha$-BocLys)$_{0.5}$]$_n$

According to the same procedure as described in Example 1, the ester form of the title polyphosphazene compound, [NP(MPEG550)$_{1.5}$(N$^\alpha$-BocLysEt)$_{0.5}$] was prepared (75% yield) using hexachlorocyclotriphosphazene ([NPCl$_2$]$_3$, 11.54 g, 100 mmol), methoxypoly(ethylene glycol) with an average molecular weight of 550 (MPEG550, 82.5 g, 150 mmol), trimethylamine (80.0 ml, 600 mmol), and N$^\varepsilon$-BocLysEt (20.5 g, 75 mmol). This synthetic derivative (10 g, 10 mmol) and NaOH (0.4 g, 10 mmol) were dissolved in methanol and then subjected to hydrolysis at ambient temperature for 4 h. Complete hydrolysis was confirmed by using proton NMR, and then the solution was subjected to vacuum evaporation to obtain a solid state polymer, which was dissolved in distilled water and acidified to pH=3 by organic acid. This acidic polymer solution was extracted with chloroform or dichloromethane three times. The organic layer was dried using anhydrous sodium bicarbonate and then subjected to vacuum evaporation to obtain the title compound (95% yield).

Composition: C$_{86}$H$_{174}$N$_4$O$_{43}$P$_2$
Elemental analysis data (%): C, (51.02); H, (8.94); N, (2.91). Theoretical value: (51.28); H, (8.71); N, (2.78).
$^1$H-NMR spectra (CDCl$_3$) (δ, ppm): 1.32 (s, 4.5H, Boc-CH$_3$), 1.39-1.98 (br, 6.00H, Lys-CH$_2$), 2.90 (br, 2.0H, Lys-ε-CH$_2$), 3.38 (s, 3.0H, MPEG550-OCH$_3$), 3.65 (br, 66.0H, MPEG550-OCH$_2$CH$_2$), 4.45 (m, 1.0H, Lys-CH).

EXAMPLE 8

Synthesis of [NP(MPEG550)(AE)]$_n$

According to the same procedure as described in Example 1, PEGylated polyphosphazene intermediate was prepared using hexachlorocyclotriphosphazene ([NPCl$_2$]$_3$, 2.0 g, 5.72 mmol), the catalytic aluminium chloride (AlCl$_3$, 7.0 wt %), methoxypoly(ethylene glycol) with an average molecular weight of 550 (MPEG550, 9.48 g, 17.2 mmol), and sodium metal (0.59 g, 25.7 mmol). In the meantime, 2-aminoethanol (AE, 1.30 g, 21.3 mmol) and sodium hydride (0.61 g, 25.4 mmol) were reacted in dried tetrahydrofuran (50 ml) at ambient temperature for 5 h to obtain a yellow precipitate of sodium salt of 2-aminoethanol, which was washed thoroughly with ethyl ether and then dissolved in dimethyl sulfoxide (50 ml). The resultant solution was added to the above-mentioned PEGylated polyphosphazene intermediate, and the reaction mixture was further reacted for 24 h at 50° C. The reaction mixture was filtered to remove the byproduct sodium chloride and the filtrate was subjected to dialysis using cellulose membrane (MWCO: 3.5 kDa) and freeze drying to obtain a new polyphosphazene carrier polymer in 70% yield.

Composition: C$_{27}$H$_{57}$N$_2$O$_{14}$P.H$_2$O
Elemental analysis data (%): C, (47.38); H, (8.61); N, (3.95). Theoretical value: (47.45); H, (8.64); N, (4.10).
$^1$H-NMR spectra (CDCl$_3$) (δ, ppm): 3.26 (s, 3H, OCH$_3$ of MPEG), 3.50-3.52 (m, 4H, (CH$_2$)$_2$ of aminoethanol), 3.54-3.81 (brm, 46H, CH$_2$ of MPEG), 3.83-4.10 (brm, 2H, —P—O—CH$_2$— of MPEG).
$^{31}$P-NMR spectra: (CDCl$_3$, ppm): δ −2.66 (O—P—O).

EXAMPLE 9

Synthesis of [NP(MPEG750)(AE)]$_n$

According to the same procedure as described in Example 8, the desired product of the title polyphosphazene compound was prepared using hexachlorocyclotriphosphazene ([NPCl$_2$]$_3$, 2.0 g, 5.72 mmol), catalytic aluminum chloride (AlCl$_3$, 7.0 wt %), methoxypoly(ethylene glycol) with an average molecular weight of 750 (MPEG750, 12.9 g, 17.2 mmol), sodium metal (0.59 g, 25.7 mmol), 2-aminoethanol (1.30 g, 21.3 mmol) and sodium hydride (0.61 g, 25.4 mmol) in 78% yield.

Composition: C$_{35}$H$_{73}$N$_2$O$_{18}$P.H$_2$O.
Elemental analysis data (%): C, (48.02); H, (8.96); N, (3.55). Theoretical value: (48.89); H, (8.73); N, (3.26).
$^1$H-NMR spectra (CDCl$_3$) (δ, ppm): 3.41 (s, 3H, OCH$_3$ of MPEG), 3.49-3.53 (m, 4H, (CH$_2$)$_2$ of aminoethanol), 3.57-3.83 (brm, 62H, CH$_2$ of MPEG), 3.83-4.05 (brm, 2H, —P—O—CH$_2$— of MPEG).
$^{31}$P-NMR spectra: (CDCl$_3$, ppm): δ −3.95 (O—P—O).

Synthesis of Anticancer Drug-Linker Precursor

EXAMPLE 10

Synthesis of 2'-aconitic docetaxel NHS ester

Aconitic anhydride (3.12 g, 20 mmol), docetaxel (8.03 g, 10 mmol) and a catalyst DPTS (dimethylaminopyridine/p-toluenesulfonic acid) (6.0 g, 20 mmol) were vacuum-dried for 4 h and cooled to −10° C. and then completely dissolved in dried tetrahydrofuran (100 ml). To this solution was slowly added DIC (N,N'-diisopropylcarbodiimide) (2.5 g, 20 mmol) dissolved also in dried tetrahydrofuran. The mixed reaction solution was reacted for 6 h at −10° C. and then for 6 to 12 h at 0° C. The progress of the reaction was monitored by TLC using a solvent mixture of dichloromethane:methanol (95:5) until no free docetaxel is detected. After confirmed completion of the reaction, excess amount of NHS (N-hydroxysuccinimide) (11.5 g, 100 mmol) and a large excess of basic DIPEA(diisopropyl ethyl amine) were added to the above reaction solution and the reaction mixture was further reacted for 12 h. The reaction mixture was finally subjected to vacuum evaporation to obtain a solid polymer product, which was dissolved in small amount of ethanol (50 ml) and then a large amount of water (950 ml) was added thereto for recrystallization at 0° C. for 3 h. The supernatant water layer is removed to obtain brown oily product, which was dissolved in chloroform or dichloromethane for washing successively with salt solution (pH=7), citric acid solution (pH=2), sodium bicarbonate solution (pH=9) and finally with salt solution. The final organic solution was dried using anhydrous magnesium sulfate and then vacuum dried to obtain finally the precursor composed of 2'-acconitic-docetaxel-NHS ester.

Composition: $C_{53}H_{60}N_2O_{21}$

Elemental analysis data (%): C, (60.07); H, (5.86); N, (2.71). Theoretical value: (59.99); H, (5.70); N, (2.64).

$^1$H-NMR spectra (CDCl$_3$) (δ, ppm): 1.13 ppm (s, 3H, C17-CH$_3$), 1.24 ppm (s, 3H, C16-CH$_3$), 1.34 ppm (s, 9H, C60-t Bu), 1.75 ppm (s, 3H, C19-CH$_3$), 1.96 ppm (s, 3H, C18-CH$_3$), 2.18 ppm (d, 2H, C14-CH$_2$), 2.43 ppm (s, 3H, C22-CH$_3$), 2.64 (t, 4H, NHS—CH$_2$CH$_2$), 2.92 (s, 2H, aconitic-CH$_2$), 4.21 ppm (d, 1H, C20-CH$_a$), 4.24 ppm (m, 1H, C7-CH), 4.32 ppm (d, 1H, C20-CH$_b$), 4.95 ppm (dd, 1H, C5CH), 5.23 ppm (d, 1H, C10-CH), 5.40 ppm (d, 1H, C30-CH), 5.69 ppm (d, 1H, C2-CH), 6.40-6.68 (m, 1H, aconitic-CH), 7.51 ppm (m, 2H, C33, C27-CH), 7.53 (m, 6H, C32, C34-CH; C31, C35-CH; C26, C28-CH), 8.12 (d, 2H, C25, C29-CH).

EXAMPLE 11

Synthesis of 2'-aconitic paclitaxel-NHS ester

According to the same procedure as described in Example 10, the desired product of the precursor composed of 2'-acconitic-paclitaxel-NHS ester was prepared using aconitic anhydride (3.12 g, 20 mmol), paclitaxel (8.53 g, 10 mmol), DPTS (5.88 g, 20 mmol), NHS (11.5 g, 100 mmol), DIC (2.52 g, 20 mmol) and DIPEA (10 ml).

Composition: $C_{55}H_{58}N_2O_{19}$

Elemental analysis data (%): C, (61.90); H, (5.75); N, (2.80). Theoretical value: (62.85); H, (5.56); N, (2.67).

$^1$H-NMR spectra (CDCl$_3$) (δ, ppm): 1.13 ppm (s, 3H, C17-CH$_3$), 1.24 ppm (s, 3H, C16-CH$_3$), 1.34 ppm (s, 9H, C60-t Bu), 1.75 ppm (s, 3H, C19-CH$_3$), 1.96 ppm (s, 3H, C18-CH$_3$), 2.18 ppm (d, 2H, C14-CH$_2$), 2.43 ppm (s, 3H, C22-CH$_3$), 2.64 (t, 4H, NHS—CH$_2$CH$_2$), 2.92 (s, 2H, aconitic-CH$_2$), 4.21 ppm (d, 1H, C20-CH$_a$), 4.24 ppm (m, 1H, C7-CH), 4.32 ppm (d, 1H, C20-CH$_b$), 4.95 ppm (dd, 1H, C5-CH), 5.23 ppm (d, 1H, C10-CH), 5.40 ppm (d, 1H, C30-CH), 5.69 ppm (d, 1H, C2-CH), 6.40-6.68 (m, 1H, aconitic-CH), 7.51 ppm (m, 2H, C33, C27-CH), 7.53 (m, 6H, C32, C34-CH; C31, C35-CH; C26, C28-CH), 8.12 (d, 2H, C25, C29-CH).

EXAMPLE 12

Synthesis of 2'-aconitic camptothecin-NHS ester

According to the same procedure as described in Example 10, the desired product of the precursor composed of 2'-acconitic-camptothecin-NHS ester was prepared using aconitic anhydride (3.12 g, 20 mmol), camptothecin (3.48 g, 10 mmol), DPTS (5.88 g, 20 mmol), NHS (11.5 g, 100 mmol), DIC (2.52 g, 20 mmol) and DIPEA (10 ml).

Composition: $C_{30}H_{23}N_3O_{11}$

Elemental analysis data (%): C, (60.29); H, (3.98); N, (6.57). Theoretical value: (59.90); H, (3.85); N, (6.99).

$^1$H-NMR spectra (CDCl$_3$) (δ, ppm): 0.9 (t, 3H, C18-CH$_3$), 2.0 (m, 2H, C19-CH$_2$), 2.64 (t, 4H, NHS—CH$_2$CH$_2$), 2.92 (s, 2H, aconitic-CH$_2$), 4.20 (d, 2H, C5-CH$_2$), 4.76 (m, 2H, C22-CH$_2$), 6.40-6.68 (m, 1H, aconitic-CH), 6.70 (s, 1H, C14-CH), 7.59 (s, 1H, C11-CH), 7.80 (m, 2H, C12-CH; C7-CH), 8.0 (m, 2H, C9-CH; C12-CH).

EXAMPLE 13

Synthesis of 2'-aconitic glycamptothecin t-Boc-glycine (0.5 g, 2.85 mmol) and camptothecin(CPT) (0.5 g, 1.43 mmol) were dissolved in anhydrous methylenechloride (20 ml) and thereto DIPC (0.36 ml, 2.85 mmol) and DMAP (0.31 g, 2.53 mmol) were added. The mixture solution was reacted by stirring at room temperature for 16 h. The resulting mixture was extracted by shaking with dilute aqueous hydrochloric acid solution (pH=2). The aqueous layer was separated and dried using anhydrous magnesiun sulfate, followed by vacuum drying to obtain t-Boc-glycamptothecin. This intermediate was reacted in the mixture of methylenechloride and trifluoroacetic acid (10 ml/10 ml) for 1 h to remove t-Boc group, and the resultant camptothecin-gly-NH$_2$ and cis-aconitic anhydride (0.57 g, 3.63 mmol) are reacted in dimethylformamide solvent (2 ml) at 0° C. for 16 h. To the reaction mixture excess amount of ethyl ether was added to precipitate the camptothecin precursor, which was filtered and vacuum-dried to obtain 2'-aconitic-glycamptothecin in 80% yield.

Composition: $C_{28}H_{23}N_3O_{10}$

Elemental analysis data (%): C, (59.72); H, (4.01); N, (7.39). Theoretical value: (59.84); H, (4.09); N, (7.48).

$^1$H-NMR spectra (CDCl$_3$) (δ, ppm): 0.88-0.93 (brm, 3H, —CH$_3$ of CPT-C18), 2.12-2.16 (m, 2H, —CH$_2$ of CPT-C19), 2.86 (s, 2H, —CH$_2$ of cis-aconitate), 3.92-4.42 (brm, 2H, —CH$_2$ of glycine), 5 0.27 (brs, 2H, —CH$_2$ of CPT-C5), 5.49 (brs, 2H, —CH$_2$ of CPT-C22), 5.97 (s, 1H, =CH of cis-aconitate), 7.18-7.21 (m, 1H, =CH of CPT-C14), 7.69-7.72 (m, 1H, =CH of CPT-C11), 7.84-7.89 (m, 1H, =CH of CPT-C10) 8.10-8.21 (m, 2H, =CH of CPT-C12 and C9), 8.68 (brs, 1H, =CH of CPT-C7), 12.3-12.8 (brs, —COOH of cis-aconitatic acid).

Synthesis of Polyphosphazene-Anticancer Drug Conjugates

EXAMPLE 14

Synthesis of [NP(MPEG550)$_{1.5}$(LysEt-2'-aconitic-docetaxel)$_{0.5}$]$_n$

The polyphosphazene compound (4.85 g. 5.0 mmol) obtained in Example 1 was dissolved in methylene chloride in a reaction flask, which was cooled using ice bath. The 2'-aconitic-docetaxel-NHS ester obtained in Example 8 dissolved also in methylene chloride was added to the reaction flask and the reaction mixture was reacted for 12 h at low temperature (0-5° C.). After 12 h reaction, the reaction mixture was subjected to vacuum evaporation and the residue was dissolved in a small amount of ethanol, followed by addition of a large excess amount of water for recrystallization, which was repeated twice. The remaining insoluble impurities were removed using membrane filter and the filtrate was washed five times with 30% ethanol aqueous solution and then five times with pure water, followed by fractionation using ultra-membrane and freeze-dry to obtain the final polyphosphazene-docetaxel conjugate, [NP(MPEG550)$_{1.5}$(LysEt-2'-aconitic-docetaxel)$_{0.5}$]$_n$ in 90% yield.

Composition: $C_{132}H_{225}N_5O_{59}P_2$.

Elemental analysis data (%): C, (53.62); H, (7.92); N, (2.67). Theoretical value: (54.89); H, (7.85); N, (2.42).

$^1$H-NMR spectra (CDCl$_3$) (δ, ppm): 1.13 ppm (s, 1.5H, C17-CH$_3$), 1.24 ppm (s, 1.5H, C16-CH$_3$), 1.34 ppm (bs, 4.1H, C60-t Bu), 1.75 ppm (s, 1.5H, C19-CH$_3$), 1.96 ppm (s, 1.5H, C18-CH$_3$), 2.18 ppm (d, 1.0H, C14-CH$_2$), 2.43 ppm (s, 1.5H, C22-CH$_3$), 4.21 ppm (d, 0.5H, C20-CH$_a$), 4.24 ppm (m, 0.5H, C7-CH), 4.32 ppm (d, 0.5H, C20-CH$_b$), 4.95 ppm (dd, 0.5H, C5-CH), 5.23 ppm (d, 0.5H, C10-CH), 5.40 ppm (d, 0.5H, C30-CH), 5.69 ppm (d, 0.5H, C2-CH), 7.51 ppm (m, 1.0H, C33, C27-CH), 7.53 (m, 3.0H, C32, C34-CH; C31, C35-CH; C26, C28-CH), 8.12 (d, 0.6H, C25, C29-CH), 1.24 (s, 1.5H, Lys-OCH$_2$CH$_3$), 1.29 (bs, 1H, Lys-CH$_2$), 1.55 ppm (bs, 1H, Lys-CH$_2$), 1.80 (bs, 1H, Lys-CH$_2$), 2.90 (br, 1H, Lys-e-CH$_2$), 3.38 ppm (s, 4.50H, CH$_3$O—, PEG), and 3.63 ppm (m, 66.0H, —CH$_2$CH$_2$—O—), 4.4 (s, 0.51H, Lysine-CH).

$^{31}$P-NMR spectra: (CDCl$_3$, ppm): δ −0.014 (s), δ −5.551 (s).

EXAMPLE 15

Synthesis of [NP(MPEG550)$_{1.5}$(LysEt)$_{0.2}$(LysEt-2'-aconitic-docetaxel)$_{0.3}$]$_n$ According to the same procedure as described in Example 14, the desired title product was prepared using the polyphosphazene compound of Example 1 (9.7 g, 10 mmol), the precursor, 2'-aconitic docetaxel NHS ester (3.18 g, 3.0 mmol) of Example 11 and DIPEA (5 ml) in 90% yield.

Composition: C$_{112.4}$H$_{203}$N$_{4.6}$O$_{51.8}$P$_2$.

Elemental analysis data (%): C, (53.48); H, (8.31); N, (2.64). Theoretical value: (53.79); H, (8.15); N, (2.57).

$^1$H-NMR spectra (CDCl$_3$) (δ, ppm): 1.13 ppm (s, 0.9H, C17-CH$_3$), 1.24 ppm (s, 0.9H, C16-CH$_3$), 1.34 ppm (bs, 3.31H, C60-t Bu), 1.75 ppm (s, 0.9H, C19-CH$_3$), 1.96 ppm (s, 0.9H, C18-CH$_3$), 2.18 ppm (d, 0.6H, C14-CH$_2$), 2.43 ppm (s, 0.9H, C22-CH$_3$), 4.21 ppm (d, 0.3H, C20-CH$_a$), 4.24 ppm (m, 0.3H, C7-CH), 4.32 ppm (d, 0.3H, C20-CH$_b$), 4.95 ppm (dd, 0.31H, C5-CH), 5.23 ppm (d, 0.3H, C10-CH), 5.40 ppm (d, 0.3H, C30-CH), 5.69 ppm (d, 0.3H, C2-CH), 7.51 ppm (m, 0.6H, C33, C27-CH), 7.53 (m, 1.8H, C32, C34-CH; C31, C35-CH; C26, C28-CH), 8.12 (d, 0.6H, C25, C29-CH), 1.24 (s, 1.5H, Lys-OCH$_2$CH$_3$), 1.29 (bs, 1H, Lys-CH$_2$), 1.55 ppm (bs, 1H, Lys-CH$_2$), 1.80 (bs, 1H, Lys-CH$_2$), 2.90 (br, 1H, Lys-e-CH$_2$), 3.38 ppm (s, 4.50H, CH$_3$O—, PEG), and 3.63 ppm (m, 66.0H, —CH$_2$CH$_2$—O—), 4.4 (s, 0.51H, Lysine-CH).

$^{31}$P-NMR spectra: (CDCl$_3$, ppm): δ −0.014 (s), δ −5.551 (s).

EXAMPLE 16

[NP(MPEG750)$_{1.5}$(LysEt)$_{0.2}$(LysEt-2'-aconitic-docetaxel)$_{0.3}$]$_n$

According to the same procedure as described in Example 14, the desired title product was prepared using the polyphosphazene compound of Example 2 (12.3 g, 10 mmol), the precursor, 2'-aconitic docetaxel NHS ester (5.3 g, 5.0 mmol) of Example 11 and DIPEA (10 ml) in 89% yield.

Composition: C$_{136.4}$H$_{251}$N$_{4.6}$O$_{63.8}$P$_2$.

Elemental analysis data (%): C, (53.27); H, (8.45); N, (2.31). Theoretical value: (53.92); H, (8.33); N, (2.12).

$^1$H-NMR spectra (CDCl$_3$) (δ, ppm): 1.13 ppm (s, 0.9H, C17-CH$_3$), 1.24 ppm (s, 0.9H, C16-CH$_3$), 1.34 ppm (bs, 3.31H, C60-t Bu), 1.75 ppm (s, 0.9H, C19-CH$_3$), 1.96 ppm (s, 0.9H, C18-CH$_3$), 2.18 ppm (d, 0.6H, C14-CH$_2$), 2.43 ppm (s, 0.9H, C22-CH$_3$), 4.21 ppm (d, 0.3H, C20-CH$_a$), 4.24 ppm (m, 0.3H, C7-CH), 4.32 ppm (d, 0.3H, C20-CH$_b$), 4.95 ppm (dd, 0.31H, C5-CH), 5.23 ppm (d, 0.3H, C10-CH), 5.40 ppm (d, 0.3H, C30-CH), 5.69 ppm (d, 0.3H, C2-CH), 7.51 ppm (m, 0.6H, C33, C27-CH), 7.53 (m, 1.8H, C32, C34-CH; C31, C35-CH; C26, C28-CH), 8.12 (d, 0.6H, C25, C29-CH), 1.24 (s, 1.5H, Lys-OCH$_2$CH$_3$), 1.29 (bs, 1H, Lys-CH$_2$), 1.55 ppm (bs, 1H, Lys-CH$_2$), 1.80 (bs, 1H, Lys-CH$_2$), 2.90 (br, 1H, Lys-ε-CH$_2$), 3.38 ppm (s, 4.50H, CH$_3$O—, PEG), and 3.63 ppm (m, 98.0H, —CH$_2$CH$_2$O—), 4.0 (bs, 4H, MPEG 750-CH$_2$), 4.51 (s, 0.51H, Lysine-CH).

$^{31}$P-NMR spectra: (CDCl$_3$, ppm): δ −0.014 (s), δ −5.551 (s).

EXAMPLE 17

[NP(MPEG1000)$_{1.5}$(LysEt)$_{0.2}$(LysEt-2'-aconitic-docetaxel)$_{0.3}$]$_n$

According to the same procedure as described in Example 14, the desired title product was prepared using the polyphosphazene compound of Example 3 (15.6 g, 10 mmol), the precursor, 2'-aconitic docetaxel NHS ester (5.3 g, 5.0 mmol) of Example 11 and DIPEA (10 ml) in 89% yield.

Composition: C$_{172.4}$H$_{323}$N$_{4.6}$O$_{48.2}$P$_2$.

Elemental analysis data (%): C, (53.71); H, (8.74); N, (2.01). Theoretical value: (54.04); H, (8.50); N, (1.68).

$^1$H-NMR spectra (CDCl$_3$) (δ, ppm): 1.13 ppm (s, 0.9H, C17-CH$_3$), 1.24 ppm (s, 0.9H, C16-CH$_3$), 1.34 ppm (bs, 3.31H, C60-t Bu), 1.75 ppm (s, 0.9H, C19-CH$_3$), 1.96 ppm (s, 0.9H, C18-CH$_3$), 2.18 ppm (d, 0.6H, C14-CH$_2$), 2.43 ppm (s, 0.9H, C22-CH$_3$), 4.21 ppm (d, 0.3H, C20-CH$_a$), 4.24 ppm (m, 0.3H, C7-CH), 4.32 ppm (d, 0.3H, C20-CH$_b$), 4.95 ppm (dd, 0.31H, C5-CH), 5.23 ppm (d, 0.3H, C10-CH), 5.40 ppm (d, 0.3H, C30-CH), 5.69 ppm (d, 0.3H, C2-CH), 7.51 ppm (m, 0.6H, C33, C27-CH), 7.53 (m, 1.8H, C32, C34-CH; C31, C35-CH; C26, C28-CH), 8.12 (d, 0.6H, C25, C29-CH), 1.24 (s, 1.5H, Lys-OCH$_2$CH$_3$), 1.29 (bs, 1H, Lys-CH$_2$), 1.55 ppm (bs, 1H, Lys-CH$_2$), 1.80 (bs, 1H, Lys-CH$_2$), 2.90 (br, 1H, Lys-ε-CH$_2$), 3.38 ppm (s, 4.50H, MPEG-CH$_3$O—), and 3.63 ppm (m, 128H, MPEG-CH$_2$CH$_2$O), 4.0 (bs, 4H, MPEG1000-CH$_2$), 4.51 (s, 0.51H, Lysine-CH).

$^{31}$P-NMR spectra: (CDCl$_3$, ppm): δ −0.014 (s), δ −5.551 (s).

EXAMPLE 18

Synthesis of [NP(MPEG550)$_{1.0}$(LysEt)$_{0.5}$(LysEt-2'-aconitic-docetaxel)$_{0.5}$]$_n$ According to the same procedure as described in Example 14, the desired title product was prepared using the polyphosphazene compound of Example 5 (7.7 g, 10 mmol), the precursor, 2'-aconitic docetaxel NHS ester (6.36 g, 6.0 mmol) of Example 10 and DIPEA (10 ml) in 89% yield.

Composition: C$_{115}$H$_{191}$N$_7$O$_{48}$P$_2$.

Elemental analysis data (%): C, (54.92); H, (8.01); N, (3.99). Theoretical value: (55.21); H, (7.70); N, (3.92).

$^1$H-NMR spectra (CDCl$_3$) (δ, ppm): 1.13 ppm (s, 0.9H, C17-CH$_3$), 1.24 ppm (s, 0.9H, C16-CH$_3$), 1.34 ppm (bs, 3.31H, C60-t Bu), 1.75 ppm (s, 0.9H, C19-CH$_3$), 1.96 ppm (s, 0.9H, C18-CH$_3$), 2.18 ppm (d, 0.6H, C14-CH$_2$), 2.43 ppm (s, 0.9H, C22-CH$_3$), 4.21 ppm (d, 0.3H, C20-CH$_a$), 4.24 ppm (m, 0.3H, C7-CH), 4.32 ppm (d, 0.3H, C20-CH$_b$), 4.95 ppm (dd, 0.31H, C5-CH), 5.23 ppm (d, 0.3H, C10-CH), 5.40 ppm (d, 0.3H, C30-CH), 5.69 ppm (d, 0.3H, C2-CH), 7.51 ppm (m, 0.6H, C33, C27-CH), 7.53 (m, 1.8H, C32, C34-CH; C31, C35-CH; C26, C28-CH), 8.12 (d, 0.6H, C25, C29-CH), 1.24 (s, 3.0H, Lys-OCH$_2$CH$_3$), 1.29 (bs, 2H, Lys-CH$_2$), 1.55 ppm (bs, 2H, Lys-CH$_2$), 1.80 (bs, 2H, Lys-CH$_2$), 2.90 (br, 2H, Lys-e-CH$_2$), 3.38 ppm (s, 3.00H, CH$_3$O—, PEG), and 3.63 ppm (m, 44.0H, —CH$_2$CH$_2$—O—), 4.4 (s, 0.51H, Lysine-CH).

$^{31}$P-NMR spectra: (CDCl$_3$, ppm): δ −0.014 (s), δ −5.551 (s).

EXAMPLE 19

Synthesis of [NP(MPEG550)$_{1.5}$(GlyLysEt)}$_{0.2}$(GlyLysEt-2'-aconitic-ocetaxel)$_{0.3}$]$_n$ According to the same procedure as described in Example 14, the desired title product was prepared using the polyphosphazene compound of Example 6 (10.4 g, 10 mmol), the precursor, 2'-aconitic docetaxel NHS ester (5.3 g, 5.0 mmol) of Example 10 and DIPEA (10 ml) in 89% yield.

Composition: C$_{114.4}$H$_{206}$N$_{5.6}$O$_{52.8}$P$_2$.

Elemental analysis data (%): C, (52.98); H, (8.23); N, (3.19). Theoretical value: (53.53); H, (8.09); N, (3.06).

$^1$H-NMR spectra (CDCl$_3$) (δ, ppm): 1.13 ppm (s, 0.9H, C17-CH$_3$), 1.24 ppm (s, 0.9H, C16-CH$_3$), 1.34 ppm (bs, 3.31H, C60-t Bu), 1.75 ppm (s, 0.9H, C19-CH$_3$), 1.96 ppm (s, 0.9H, C18-CH$_3$), 2.18 ppm (d, 0.6H, C14-CH$_2$), 2.43 ppm (s, 0.9H, C22-CH$_3$), 4.21 ppm (d, 0.3H, C20-CH$_a$), 4.24 ppm (m, 0.3H, C7-CH), 4.32 ppm (d, 0.3H, C20-CH$_b$), 4.95 ppm (dd, 0.31H, C5-CH), 5.23 ppm (d, 0.3H, C10-CH), 5.40 ppm (d, 0.3H, C30-CH), 5.69 ppm (d, 0.3H, C2-CH), 7.51 ppm (m, 0.6H, C33, C27-CH), 7.53 (m, 1.8H, C32, C34-CH; C31, C35-CH; C26, C28-CH), 8.12 (d, 0.6H, C25, C29-CH), 1.24 (s, 1.5H, Lys-OCH$_2$CH$_3$), 1.29 (bs, 1H, Lys-CH$_2$), 1.55 ppm (bs, 1H, Lys-CH$_2$), 1.80 (bs, 1H, Lys-CH$_2$), 2.90 (br, 1H, Lys-e-CH$_2$), 3.38 ppm (s, 4.50H, CH$_3$O—, PEG), and 3.63 ppm (m, 66.0H, —CH$_2$CH$_2$—O—), 3.98 (bs, 2H, Gly-CH$_2$), 4.4 (s, 0.51H, Lysine-CH).

$^{31}$P-NMR spectra: (CDCl$_3$, ppm): δ −0.014 (s), δ −5.551 (s).

EXAMPLE 20

Synthesis of [NP(MPEG550)$_{1.50}$(LysEt)$_{0.2}$(LysEt-2'-succinylpaclitaxel)$_{0.3}$]$_n$ The polyphosphazene compound of Example 1 (9.7 g, 10 mmol) was reacted with 2'-succinylpaclitaxel (5.26 g, 5.0 mmol) prepared by the literature procedure (C.-M. Huang, et al, *Chem. Biol.* 2000, 7, 453-461) by esterification using DCL (2.54 g, 20 mmol) and DIPEA (10 ml) to obtain the desired title compound in 90% yield.

Composition: C$_{113.6}$H$_{202}$N$_{4.6}$O$_{51.8}$P$_2$.

Elemental analysis data (%): C, (54.15); H, (8.26); N, (2.61). Theoretical value: (54.49); H, (8.12); N, (2.57).

$^1$H-NMR spectra (CDCl$_3$) (δ, ppm): 1.25 (s, 1.5H, Lys-OCH$_2$CH$_3$), 2.49 (br, 1.00H, suucinyl-CH$_2$), 2.90 (br, 1.00H, Lys-ε-CH$_2$), 3.38 (s, 4.50H, MPEG550-OCH$_3$), 3.65 (br, 66.0H, MPEG550-OCH$_2$CH$_2$), 1.13 (s, 12H), 1.25 (s, 12H), 1.35 (s, 36H), 1.68 (m, 8H), 1.75 (s, 12H), 1.86 (m, 8H), 1.96 (s, 12H), 2.36 (m, 20H), 2.60 (m, 4H), 3.98 (s, 8H), 4.06 (d, 8H), 4.30 (m, 12H), 4.33 (m. 8H), 4.97 (d, 4H), 5.22 (m, 4H), 5.36 (s, 4H), 5.60 (m, 4H), 5.69 (m, 8H), 6.20 (t, 4H), 7.33 (m, 8H), 7.41 (m, 8H), 7.52 (m, 8H), 7.61 (m, 4H), 7.33 (m, 4H), 8.12 (d, 8H).

$^{31}$P-NMR spectra: (CDCl$_3$, ppm): δ −0.014 (s), δ −5.551 (s).

EXAMPLE 21

Synthesis of [NP(MPEG550)$_{1.50}$(GlyLysEt-2'-succinylpaclitaxel)$_{0.50}$]$_n$ According to the same procedure as described in Example 20, the desired title product was prepared using the polyphosphazene compound of Example 6 (10.4 g, 10 mmol), 2'-succinylpaclitaxel (7.36 g, 7.0 mmol) prepared by the literature procedure (C.-M. Huang, et al, *Chem. Biol.* 2000, 7, 453-461) by esterification reaction using DCL (2.54 g, 20 mmol) and DIPEA (10 ml) to obtain the desired title compound in 80% yield.

Composition: C$_{136}$H$_{226}$N$_6$O$_{58}$P$_2$.

Elemental analysis data (%): C, (55.36); H, (7.99); N, (2.93). Theoretical value: (55.67); H, (7.76); N, (2.86).

$^1$H-NMR spectra (CDCl$_3$) (δ, ppm): 1.25 (s, 1.5H, Lys-OCH$_2$CH$_3$), 2.49 (br, 1.00H, suucinyl-CH$_2$), 2.90 (br, 1.00H, Lys-ε-CH$_2$), 3.38 (s, 4.50H, MPEG550-OCH$_3$), 3.65 (br, 66.0H, MPEG550-OCH$_2$CH$_2$), 1.13 (s, 12H), 1.25 (s, 12H), 1.35 (s, 36H), 1.68 (m, 8H), 1.75 (s, 12H), 1.86 (m, 8H), 1.96 (s, 12H), 2.36 (m, 20H), 2.60 (m, 4H), 3.98 (s, 8H), 4.06 (d, 8H), 4.30 (m, 12H), 4.33 (m. 8H), 4.97 (d, 4H), 5.22 (m, 4H), 5.36 (s, 4H), 5.60 (m, 4H), 5.69 (m, 8H), 6.20 (t, 4H), 7.33 (m, 8H), 7.41 (m, 38H), 7.52 (m, 8H), 7.61 (m, 4H), 7.33 (m, 4H), 8.12 (d, 8H)

$^{31}$P-NMR spectra: (CDCl$_3$, ppm): δ −0.014 (s), δ −5.551 (s).

EXAMPLE 22

Synthesis of [NP(MPEG550)$_{1.50}$(N$_\alpha$-BocLys)$_{0.2}$(N$_\alpha$-BocLys-docetaxel)$_{03}$]$_n$ The polyphosphazene compound of Example 7 (9.57 g. 10.0 mmol) and docetaxel (10.6 g, 10.0 mmol) are vacuum dried and then dissolved in a dried solvent of tetrahydrofuran, methylene chloride or chloroform in a reaction vessel, which was cooled in ice bath and then the catalyst DC1 (2.54 g, 20 mmol) and DIPEA (10 ml) dissolved in the same solvent were added thereto. After the reaction mixture was reacted at ice temperature for 24 h, the reaction solution was filtered at reduced pressure and the filtrate was vacuum dried. The resultant product was purified in the same way as in Example 14 to obtain the title compound in 60% yield.

Composition: C$_{113.8}$H$_{204.2}$N$_{4.6}$O$_{50.8}$P$_2$.

Elemental analysis data (%): C, (55.06); H, (7.98); N, (2.60). Theoretical value: (54.42); H, (8.19); N, (2.57).

$^1$H-NMR spectra (CDCl$_3$) (δ, ppm): 1.25 (s, 1.5H, Lys-OCH$_2$CH$_3$), 2.49 (br, 1.00H, suucinyl-CH$_2$), 2.90 (br, 1.00H, Lys-ε-CH$_2$), 3.38 (s, 4.50H, MPEG550-OCH$_3$), 3.65 (br, 66.0H, MPEG550-OCH$_2$CH$_2$), 1.13 (s, 12H), 1.25 (s, 12H), 1.35 (s, 36H), 1.68 (m, 8H), 1.75 (s, 12H), 1.86 (m, 8H), 1.96 (s, 12H), 2.36 (m, 20H), 2.60 (m, 4H), 3.98 (s, 8H), 4.06 (d, 8H), 4.30 (m, 12H), 4.33 (m. 8H), 4.97 (d, 4H), 5.22 (m, 4H), 5.36 (s, 4H), 5.60 (m, 4H), 5.69 (m, 8H), 6.20 (t, 4H), 7.33 (m, 8H), 7.41 (m, 8H), 7.52 (m, 8H), 7.61 (m, 4H), 7.33 (m, 4H), 8.12 (d, 8H).

$^{31}$P-NMR spectra: (CDCl$_3$, ppm): δ −0.014 (s), δ −5.551 (s).

EXAMPLE 23

Synthesis of [NP(MPEG550)$_{1.5}$(LysEt)$_{0.2}$(LysEt-2'-aconitic-camptothecin)$_{0.3}$]$_n$ The polyphosphazene compound of Example 1 (9.7 g, 10 mmol) and 2'-aconitic-amptothecin-NHS ester (2.5. g, 5.03 mmol) of Example 12 were reacted according to the same method of Example 14 the required title compound was obtained in 75% yield.

Composition: $C_{98.6}H_{180.8}N_{5.2}O_{45.8}P_2$.

Elemental analysis data (%): C, (52.61); H, (8.42); N, (3.34). Theoretical value: (53.01); H, (8.16); N, (3.26).

$^1$H-NMR spectra (CDCl$_3$) (δ, ppm): 0.9 (t, 3H, C18-CH3), 2.0 (m, 2H, C19-CH$_2$), 2.64 (t, 4H, NHS—CH$_2$CH$_2$), 2.92 (s, 2H, aconitic-CH$_2$), 4.20 (d, 2H, C5-CH$_2$), 4.76 (m, 2H, C22-CH$_2$), 6.40-6.68 (m, 1H, aconitic-CH), 6.70 (s, 1H, C14-CH), 7.59 (s, 1H, C11-CH), 7.80 (m, 2H, C12-CH; C7-CH), 8.0 (m, 2H, C9-CH; C12-CH), 1.24 (s, 1.5H, Lys-OCH$_2$CH$_3$), 1.29 (bs, 1H, Lys-CH$_2$), 1.55 ppm (bs, 1H, Lys-CH$_2$), 1.80 (bs, 39 1H, Lys-CH$_2$), 2.90 (br, 1H, Lys-e-CH$_2$), 3.38 ppm (s, 4.50H, CH$_3$O—, PEG), and 3.63 ppm (m, 66.0H, —CH$_2$CH$_2$—O—), 4.4 (s, 0.51H, Lysine-CH).

$^{31}$P-NMR spectra: (CDCl$_3$, ppm): δ −0.014 (s), δ −5.551 (s).

EXAMPLE 24

Synthesis of [NP(MPEG550)(LysEt)(aconitic-glycylcamptothecin)]$_n$

According to the same procedure as described in Example 14, the desired title product was prepared using the polyphosphazene compound of Example 5 (0.5 g, 0.25 mmol) and the precursor, 2'-aconitic-glycamptothecin (0.17 g, 0.25 mmol) of Example 13 and DIPEA (10 ml) in 85% yield.

Composition: $C_{111}H_{191}N_7O_{50}P_2$.

$^1$H-NMR spectra (CDCl$_3$) (δ, ppm): 0.89-0.92 (brm, 3H, —CH$_3$ of CPT-C18), 1.13-1.58 (brm, 6H, —CH$_2$ of lysine), 2.12-2.17 (brm, 2H, —CH$_2$ of CPT-C-19), 3.01 (s, 2H, —CH$_2$ of cis-aconitate), 3.21 (s, 9H, —OCH$_3$ of MPEG), 3.34-3.54 (brm, 144H, —CH$_2$-CH$_2$ of MPEG), 3.94-4.41 (brm, 5H, —CH$_2$ of glycine, P—NH—CH$_2$ of lysine and =CH of cis-aconitate), 5.29 (brs, 2H, —CH$_2$ of CPT-C5), 5.47 (brs, 2H, —CH$_2$ of CPT-C22), 7.15-7.17 (m, 1H, =CH of CPT-C14), 7.69-7.72 (m, 1H, =CH of CPT-C11), 7.84-7.94 (m, 1H, =CH of CPT-C10) 8.10-8.21 (m, 2H, =CH of CPT-C12 and CPT-C9), 8.68 (brs, 1H, =CH of CPT-C7).

$^{31}$P-NMR (DMSO, ppm): δ −5.19 (O—P—O), 0.85 (O—P—N).

EXAMPLE 25

Synthesis of [NP(MPEG550)(AE)(ACA)Pt(dach)]$_n$

The polyphosphazene carrier polymer, [NP(MPEG550)(AE)]$_n$ (1 g, 1.5 mmol) of Example 8 was dissolved in an aqueous sodium bicarbonate solution (pH=9.0) and the linker cis-aconitic anhydride (ACA) (2.35 g, 15 mmol) was added thereto for further reaction at 4° C. for 5 h. The reaction mixture was dialyzed using a cellulose membrane (MWCO: 3.5 k Da) to obtain a new polyphosphazene intermediate bearing the linker group, [NP(MPEG550)(AE)(ACA)]$_n$. A methanol solution (20 ml) of barium hydroxide (1.33 mmol) was added to the dialyzed solution and the reaction mixture was further stirred for 5 h to convert the acidic linker group to barium salt of the polymer. The reaction solution was subjected to vacuum evaporation to dryness. The solid polymer was dissolved in distilled water (10 ml) and to this polymer solution was slowly added an aqueous solution (10 ml) of (dach)Pt(SO$_4$) (dach:trans±1,2-diaminocyclohexane) (0.49 g, 1.21 mmol) and the reaction mixture was further stirred for 3 h. After the barium sulfate precipitate was filtered out, the filtrate was dialyzed using cellulose membrane (MWCO: 3.5 kDa) and subjected to freeze dry to obtain a novel polyphosphazene-oxaliplatin conjugate drug in 74% yield.

Composition: $C_{39}H_{73}N_4O_{19}$PPt.H$_2$O

Elemental analysis data (%): C, (40.54); H, (6.34); N, (4.62). Theoretical value: (40.83); H, (6.54); N, (4.88).

$^1$H-NMR spectra (CDCl$_3$) (δ, ppm): 1.04-1.20 (brm, 4H, C-4, C-5 of dach), 1.44 (brs, 2H, C-3 of dach), 1.82-1.93 (brm, 2H, C-6 of dach), 2.02-2.52 (brm, 2H, C-1, C-2 of dach), 3.26 (s, 3H, OCH$_3$ of MPEG), 3.41-3.45 (m, 6H, CH$_2$ of cis-aconitate and aminoethanol), 3.47-3.81 (brm, 46H, —O—CH$_2$ of MPEG), 3.95-4.21 (brm, 2H, —P—O—CH$_2$— of MPEG), 4.69 (s, 1H, —C=CH— of cis-aconitate).

$^{31}$P-NMR (DMSO, ppm): −4.53 (O—P—O).

EXAMPLE 26

Synthesis of [NP(MPEG750)(AE)(ACA)Pt(dach)]$_n$

According to the same procedure as described in Example 25, the desired title product was prepared using the polyphosphazene compound of Example 9 (1.0 g, 11.91 mmol), cis-aconitic anhydride (1.86 g, 1.191 mmol), Ba(OH)$_2$.8H$_2$O (0.35 g, 1.11 mmol), and (dach)PtSO$_4$ (0.4 g, 0.99 mmol) in 72% yield.

Composition: $C_{47}H_{89}N_4O_{23}$PPt.H$_2$O

Elemental analysis data (%): C, (42.32); H, (7.64); N, (3.88). Theoretical value: (42.65); H, (6.88); N, (4.23).

$^1$H-NMR spectra (CDCl$_3$) (δ, ppm): 1.05-1.21 (brm, 4H, C-4, C-5 of dach), 1.47 (brs, 2H, C-3 of dach), 1.80-1.93 (brm, 2H, C-6 of dach), 2.01-2.45 (brm, 2H, C-1, C-2 of dach), 3.27 (s, 3H, —OCH$_3$ of MPEG), 3.41-3.45 (m, 6H, —CH$_2$ of cis-aconitate and aminoethanol), 3.50-3.72 (brm, 62H, —CH$_2$ of MPEG), 3.99-4.13 (brm, 2H, —P—O—CH$_2$ of MPEG), 4.70 (s, $_1$H, —C=CH— of cis-aconitate).

$^{31}$P-NMR (DMSO, ppm): −4.52 (O—P—O).

EXAMPLE 27

Synthesis of [NP(MPEG550)(LysEt)(ACA)Pt(dach)]$_n$

According to the same procedure as described in Example 25, the desired title product was prepared using the polyphosphazene compound of Example 5 (1.0 g, 1.28 mmol), cis-aconitic anhydride (2 g, 1.191 mmol), Ba(OH)$_2$.8H$_2$O (0.44 g, 1.39 mmol), and (dach)PtSO$_4$ (0.52 g, 1.28 mmol) in 79% yield.

Composition: $C_{45}H_{84}N_5O_{20}$PPt.H$_2$O

Elemental analysis data (%): C, (42.63); H, (6.61); N, (5.42). Theoretical value: (42.88); H, (6.83); N, (5.56).

$^1$H-NMR spectra (CDCl$_3$) (δ, ppm): 1.07-1.21 (brm, 7H, —CH$_3$, —(CH$_2$)$_2$ of lysine), 1.43-1.48 (brm, 6H, —C-3, —C-4, C-5 of dach), 1.80-1.93 (brm, 8H, —CH$_2$ lysine and —C-6 of dach), 2.02-2.26 (brm, 2H, C-1, C-2 of dach), 2.82 (brs, 2H, —CH$_2$ of cis-aconitate), 3.26 (s, 3H, —OCH$_3$ of MPEG), 3.44-3.72 (brm, 46H, —CH$_2$—CH$_2$ of MPEG), 3.96-4.03 (brm, 3H, —CH$_2$ of ethylester and —N—CH of lysine), 4.62 (s, 1H, =CH of cis-aconitate).

Measurements of Physicochemical Properties and Drug Efficacy

EXPERIMENTAL 1

Particle Size and Micelle Formation

Figure 2:
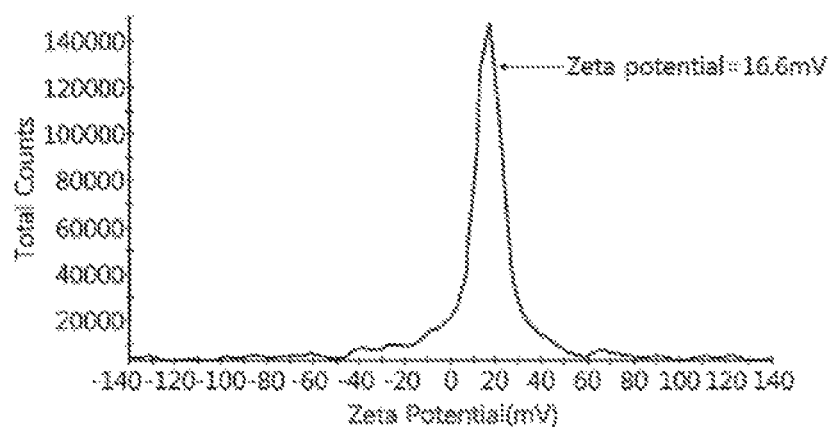
FIG. 2 shows the zeta potential measured for the cationic polyphosphazene compound of Example 1.
Figure 3:
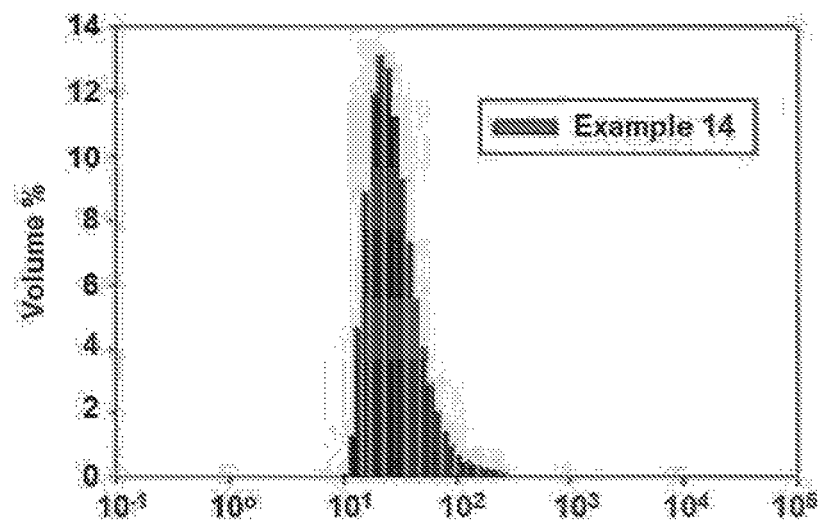
FIG. 3 shows the particle size distribution of the polyphosphazene-docetaxel conjugate of Example 14 (The mean diameter=60 nm).

The polyphosphazene carrier compound of Example 1 and the polyphosphazene-docetaxel conjugate of Example 14 were separately dissolved in distilled water (0.2%) and their particle size distributions and zeta potentials were measured by DLS (dynamic light scattering) method and the results are displayed in FIGS. 1, 2, and 3.

FIG. 1 shows the particle size distribution of the polyphosphazene carrier polymer with a mean diameter of approximately 3~4 nm, which corresponds to the particle size of a hydrodynamic volume of unassembled polymers probably due to the cationic properties of the lysine amine group of the polymer as shown in FIG. 2. However, the increased particle size of the polyphosphazene-docetaxel conjugate to 60 nm as shown in FIG. 3 clearly indicates that the conjugate drug molecules were self-assembled into larger micellar nanoparticles attributed to the amphiphilic properties of the conjugate molecules by introduction of hydrophobic docetaxel molecules into the carrier polymer. It was further confirmed that the micelle size was not changed significantly in the temperature range of 5~70° C.

EXPERIMENTAL 2

Figure 4:
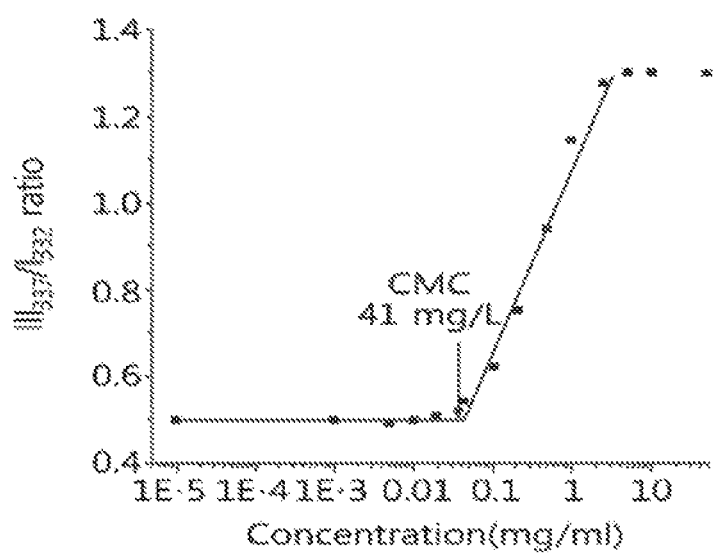
FIG. 4 shows the critical micelle concentration (CMC) of the polyphosphazene-docetaxel conjugate of Example 14 measured by the fluorescence pyrene method.

Measurement of the Critical Micelle Concentration (CMC) of Polyphosphazene-Paclitaxel Conjugate As above-mentioned, the polyphosphazene-docetaxel conjugate of the present invention forms polymeric micelles in aqueous solution. In order for such polymer-drug conjugate to be clinically useful for IV injection, the solution stability of the micelles self-assembled from the polymer-drug conjugate is critical. Such a micelle stability is expressed as "critical micelle concentration (CMC)," which is measured by several methods, but the most widely used method is "pyrene fluorescence method" (K. Kalyanasundoram, et. al, *J. Am. Chem. Soc.* 1988, 99, 2039). According to the method the CMC value of the polyphosphazene-docetaxel conjugate of the present invention was measured as in the following:

An aqueous pyrene solution ($6 \times 10^{-7}$ M) was prepared and using this solution a series of sample solutions of the polyphosphazene-paclitaxel conjugate of Example 20 was prepared in the concentration range of 5.0~0.0005% (w/w). Fluorescence spectra were measured at 339 nm ($I_{ex}$) and 390 nm ($I_{em}$) and then from the ratio of the fluorescence intensities of band I and band III, the value of CMC was determined as shown in FIG. 4.

The CMC value of the polyphosphazene-paclitaxel conjugate thus obtained was 41 mg/L, which is very low and the polymeric micelles are expected to be stable in the blood system when injected intravenously.

EXPERIMENTAL 3

Biodegradability of Polyphosphazene-Drug Conjugate

Instrument: Yonglin GPC system
Column: Waters Hydrogel HR column (1× guard, 1× linear, 2×HR2)
Eluent: water/acetonitrile (8:2) (0.5% NaNO$_3$)
Flow rate: 1 ml/min.

Figure 5:
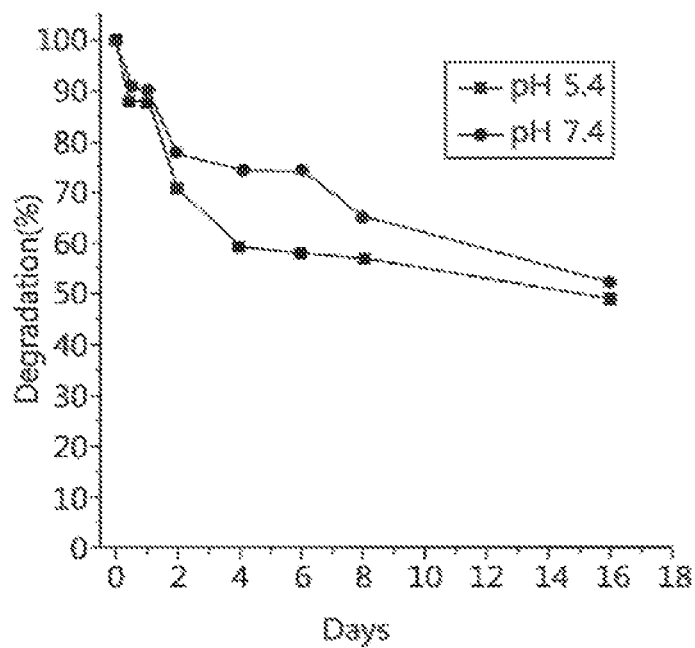
FIG. 5 shows the time dependent degradation of the polyphosphazene-paclitaxel conjugate of Example 20 at acidic pH 5.4 and neutral pH 7.4.

Two sample solutions were prepared by dissolving the polyphosphazene-paclitaxel conjugate of Example 20 (250 mg) in a buffer solution (5 ml) at pH=5.4 and in another buffer solution (5 ml) at pH=7.4. The two sample solutions were slowly shaken at 37° C. in a water bath and 500 µl of the sample solution was taken at predetermined schedule (0.5, 1, 2, 4, 6, 8, 16 day after incubation) and freeze-dried. The dried samples were dissolved in tetrahydrofuran involving 0.2% t-butyl ammonium bromide and subjected to gel permeation chromatography (GPC). From the GPC data the degradation pattern of polyphosphazene-paclitaxel conjugate drug is shown in FIG. 5.

As seen from the figure, the average molecular weight of the polyphosphazene conjugate drug rapidly decreased for first a few days, but its degradation was slow down particularly at neutral medium. The half-life of the polyphosphazene backbone in blood system was estimated to be approximately 16 days but the most encouraging factor is that the polyphosphazene backbone is continuously degradable in acidic media, which is similar to the tumor microenvironment relevant to the drug releasing kinetics. In the present invention all the final polymer products were subjected to fractionation into different molecular weights to study their biodegradation, excretion, and drug releasing kinetics.

EXPERIMENTAL 4

Tumor Targeting Properties of Polyphosphazene Compound by Imaging Study

Figure 6:
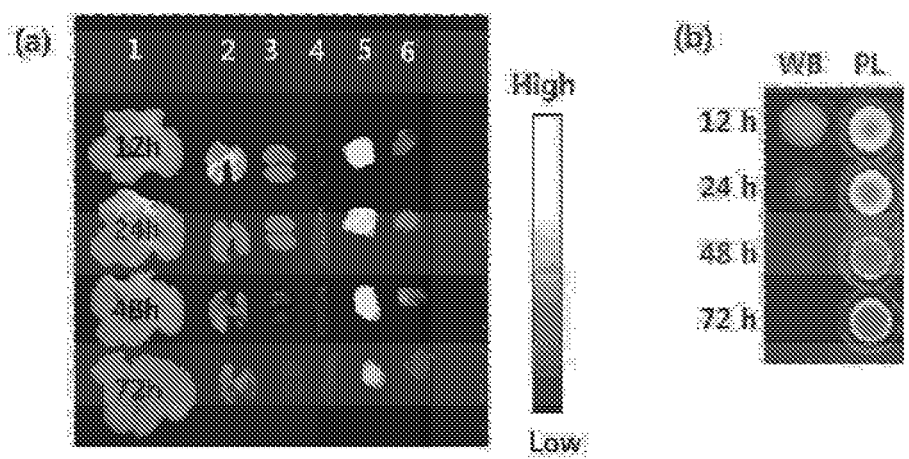
FIG. 6 (a) shows Ex vivo NIR fluorescence images of the time dependent (12 h, 24 h, 48 h, 72 h post injection) biodistributions of the Cy-labeled polyphosphazene-docetaxel conjugate of Example 14 in major organs (1: liver; 2: lung; 3: kidney; 4: spleen; 5: tumor; 6: muscle) of the mice inoculated with non-small cell lung tumor cells A549, (b) shows the time dependent NIR fluorescence images of blood (WB) and plasma (PL).

Instrument: Kodak image station 4000 mm digital imaging system (Kodak, New Haven, Conn.) Excitation and emission filter: Omega Optical, Battlebor, Vt. (ex: 560 nm, em: 700 nm) Ten eight weeks old CH$_3$/HeN nude mice (Institute of Medical Science, Tokyo) were purchased and after adaptation for a week inoculated with non-small cell lung carcinoma A549 ($1 \times 10_6$). When the tumor size was grown up to about 300 mm$^3$, the mice were classified into two groups, one group were injected with fluorescence dye Cy5.5 labeled polyphosphazene carrier compound of Example 1 and another group untreated was used as reference group. At predetermined time (12 h, 24 h, 48 h, 72 h after IV injection) the mice were sacrificed to separate the whole major organs (liver, lung, kidney, spleen, tumor, muscle), which were subjected to NIR fluorescence image study using CCD camera (Kodak Image Station 4000MM), and the results are displayed in FIG. 6.

From the fluorescence intensities of the organs in the figure, the polyphosphazene compound of Example 1 clearly showed dominant accumulation in the tumor tissue compared with other organs, despite its small particle size of 3-4 nm, which cannot afford EPR effect. Therefore, it may be presumed that the tumor selectivity of this polyphosphazene carrier polymer is due to its cationic properties attributed to the lysine free amine of the polymer and its long blood circulation due to its PEGylated structure.

EXPERIMENTAL 5

Tumor Targeting Properties of the Polyphosphazene-Docetaxel Conjugate Drug

Figure 7:
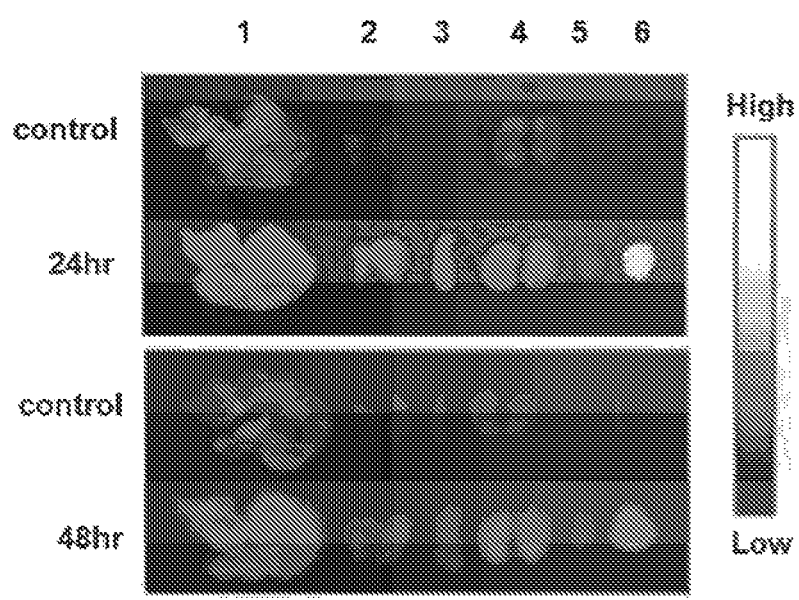
FIG. 7 shows the time dependent (24 h and 48 h post injection) biodistributions in major organs (1: liver; 2: lung; 3: spleen; 4: kidney; 5: tumor; 6: heart) of Cy-labeled polyphosphazene-docetaxel conjugate of Example 14 which is IV injected to the mice inoculated with SCC7 tumor cells.
Figure 8:
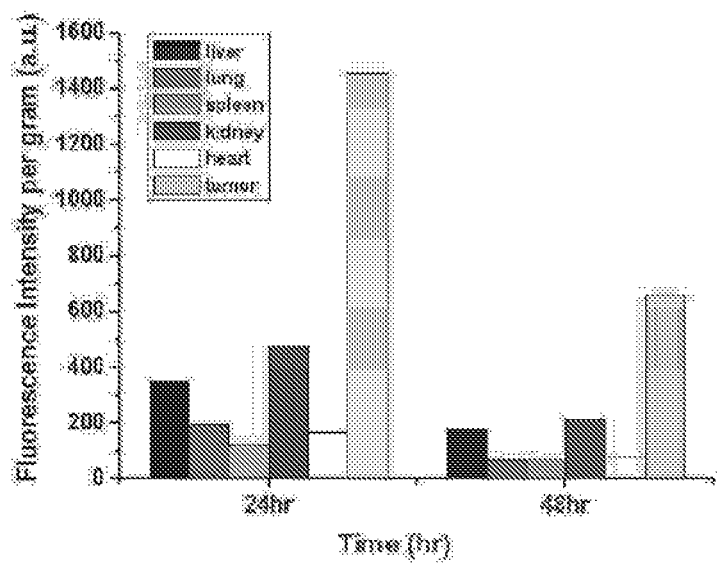
FIG. 8 shows the time dependent fluorescence intensity of each organ of the mice treated in FIG. 7 which is compared with that of each organ of the mice untreated with drug.

The polyphosphazene-docetaxel conjugate of Example 14 was labeled with Cy5.5 and its organ distributions were compared in the same way as in Experimental 4 (FIG. 7). The quantitative biodistribution data of the conjugate drug were obtained by comparison of the fluorescence intensity of each organ of the mouse treated with Cy5.5-labeled conjugate drug with that of the mouse untreated, and the results are displayed in FIG. 8.

FIG. 7 shows that the conjugate drug accumulated dominantly in tumor and in particular, its accumulation reached a maximum after 48 h post-injection probably due to EPR (Enhanced Permeability and Retention effect) effect of the larger particle size of the conjugate (60 nm) and long blood circulation. The quantitative data for biodistributions of the polyphosphazene-docetaxel conjugate drug shown in FIG. 8 clearly shows much higher tumor selectivity of the conjugate drug due to the EPR effect of its large particle size compared with the tumor selectivity of the former polyphosphazene carrier polymer attributed to its cationic properties.

EXPERIMENTAL 6

Analysis of Docetaxel Content in the Polyphosphazene-Docetaxel Conjugate

The content of the drug component in the polyphosphazene-drug conjugate may be determined by $^1$H NMR spectroscopy, UV spectroscopy, or HPLC. In the proton NMR spectroscopic method, the docetaxel content in the conjugate drug could be estimated from the ratio of integrated area of the methoxy protons at 3.4 ppm (3H —CH$_3$) of the PEG group grafted to the polymer backbone and that of the C10 protons at 7.33 ppm (C10, 2H) of docetaxel conjugated. However, both chemical shifts of the methoxy protons and docetaxel C10 protons are slightly overlapped with adjacent proton peaks, which hampers the accuracy of the integration ratio. In the HPLC method, the total amount of free docetaxel released from the conjugate drug by acidic decomposition could be measured by HPLC, but reproducible results could not be obtained.

On the other hand, reproducible results could be obtained using UV spectroscopic method, since docetaxel molecule shows a strong UV absorption at 230 nm while the polyphosphazene carrier polymer exhibits nearly no absorption at around 230 nm. Therefore, from the calibration curve measured using a solvent mixture of water and acetonitrile (1:1), in which docetaxel is completely soluble. Calibration curve was prepared by measuring UV absorption at 230 nm using the standard solution of 10.0 mg docetaxel/10 ml solvent mixture and their diluted solutions: 1 mg/ml, ½ mg/ml, etc.

EXPERIMENTAL 7

In Vitro Drug Releasing from the Polyphosphazene-Docetaxel Conjugate

Instrument: Agilent 1100 series with DAD detector (230 nm)
Column: Agilent Zobax Eclipse Plus C18 column (diameter=4.6 mm; length=150 mm, particle size=3.5 μm)
Flow rate: 1. p ml/min
Eluent composition: A: 0.1% TFA in H$_2$O; B: Acetonitrile (isocratic method)

The in vitro drug releasing experiment of the polyphosphazene-docetaxel conjugate was performed using HPLC method. The amount of released drug, docetaxel from the conjugate was determined using the calibration curve prepared in the same way as in the Experimental 6.

EXPERIMENTAL 8

In Vitro Assay of Cytotoxicity of Polyphosphazene-Paclitaxel Conjugate

Since the anticancer agent paclitaxel is well known to be clinically very efficacious against many different cancers, breast (MCF-7), ovarian (SK-OV3), non-small cell lung (A549) and stomach (SNU638) cancer cell lines were selected to test their in vitro cytotoxicity according to the literature method (SRB method) (Rita Song, et. al, *J. Control. Release* 105 (2005) 142-150).

The results are presented in the following Table 1. As is seen from the table, the IC$_{50}$ values of the polyphosphazene-paclitaxel conjugates of Example 20 and 21 much higher than the free paclitaxel, since the hydrophobic paclitaxel component is very difficult to be released from the polymeric micelle core after degradation of the polyphosphazene-paclitaxel conjugate.

TABLE 1

| | In vitro cytotoxicity of polyphosphazene-paclitaxel conjugate | | | |
|---|---|---|---|---|
| | IC$_{50}$ (nM) (mean ± SD, n = 3-4) | | | |
| Test cell lines | MCF-7 | SK-Ov3 | A-549 | SNU-638 |
| Paclitaxel | 3.47 ± 0.62 | 15.32 ± 2.6 | 6.63 ± 2.84 | 10.89 ± 0.90 |
| Example 20 | 164.8 ± 86.5 | 587.5 ± 47.8 | 170.0 ± 48.3 | 364.4 ± 201.7 |
| Example 21 | 316.7 ± 141.1 | 6964 ± 141.7 | 1543 ± 41.8 | 5411 ± 46.6 |

EXPERIMENTAL 9

Pharmacokinetic Study of the Polyphosphazene-Docetaxel Conjugate

Figure 9:
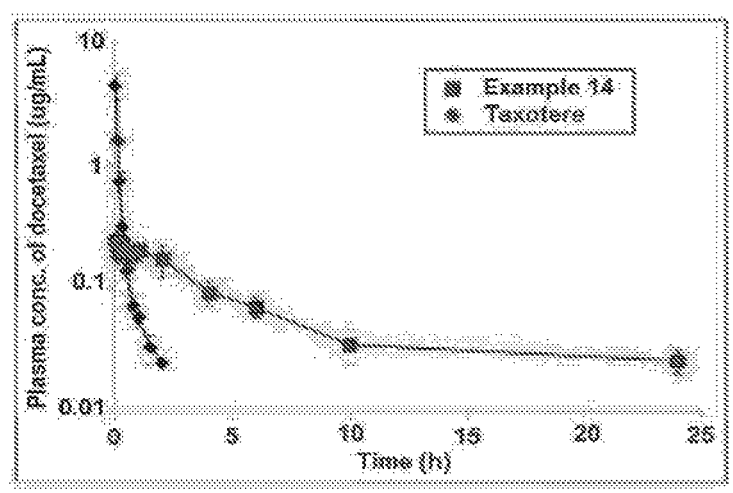
FIG. 9 shows mean plasma concentration-time profiles of docetaxel after IV injection among the results of the pharmacokinetic study of the polyphosphazene-docetaxel conjugate of Example 14 (■) and Taxotere (♦) as reference using Sprague-Dawley rat.

In order to examine the pharmacokinetic behavior of the polyphosphazene-docetaxel conjugate of Example 14 compared with the unconjugated but formulated "Taxotere" currently in clinical use, a pharmacokinetic study of the conjugate was performed using Sprague-Dawley rats according to the literature method (Jun et al., Int. J. Pharm. 422(2012) 374-380). The time dependent plasma concentration profile was displayed in FIG. 9 and the pharmacokinetic parameters were presented in Table 2.

TABLE 2

Pharmacokinetic parameters of Example 14 and Taxotere as reference.

| Pharmacokinetic parameters | Taxotere (reference) | | Example 14 | |
|---|---|---|---|---|
| | Mean | SD | Mean | SD |
| C$_0$ (μg/mL) | 8.764 | 3.221 | 0.263 | 0.051 |
| AUC$_{last}$ (μg · h/mL) | 0.651 | 0.098 | 1.192 | 0.380 |
| AUC$_{INF}$ (μg · h/mL) | 0.678 | 0.098 | 1.439 | 0.531 |
| t$_{1/2}$ (h) | 0.651 | 0.093 | 6.115 | 4.041 |
| V$_z$ (L) | 1.758 | 0.159 | 7.287 | 2.231 |
| Cl (L/h) | 1.896 | 0.255 | 0.984 | 0.311 |

EXPERIMENTAL 10

Nude Mouse Xenograft Trials of the Polyphosphazene-Docetaxel Conjugate

Figure 10:
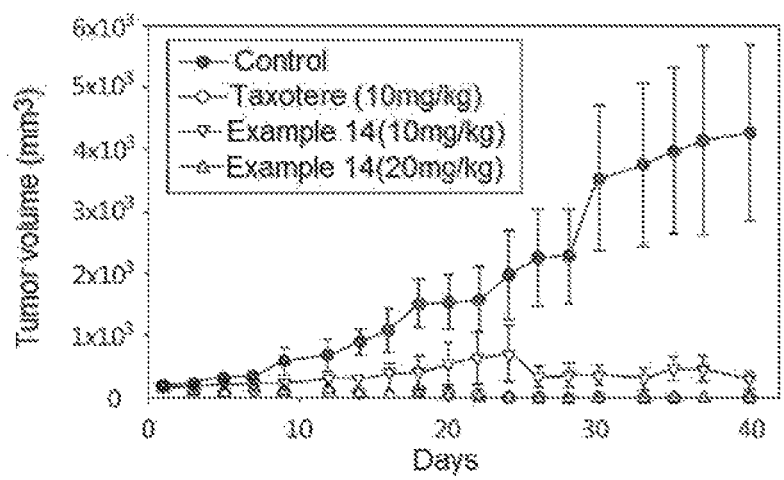
FIG. 10 shows results of the xenograft trials of the polyphosphazene-docetaxel conjugate of Example 14 using BALB/C nude mouse and MKN-28 gastric tumor cell line.
Figure 11:
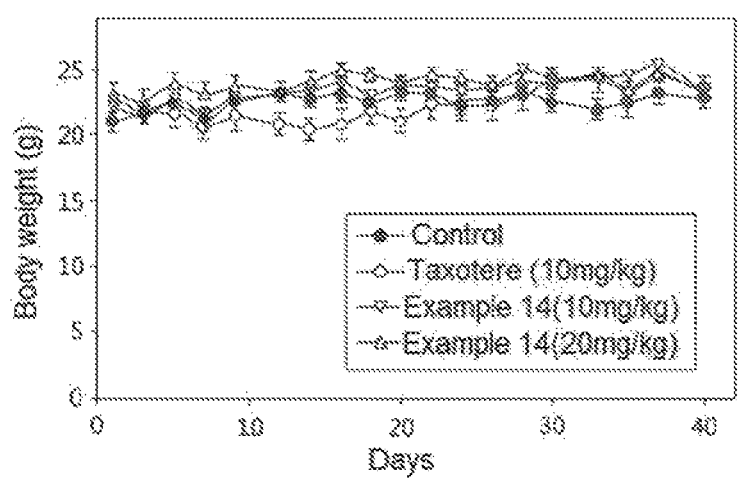
FIG. 11 shows the mouse body weight changes during the period of xenograft trials (40 days) in FIG. 10.
Figure 12:
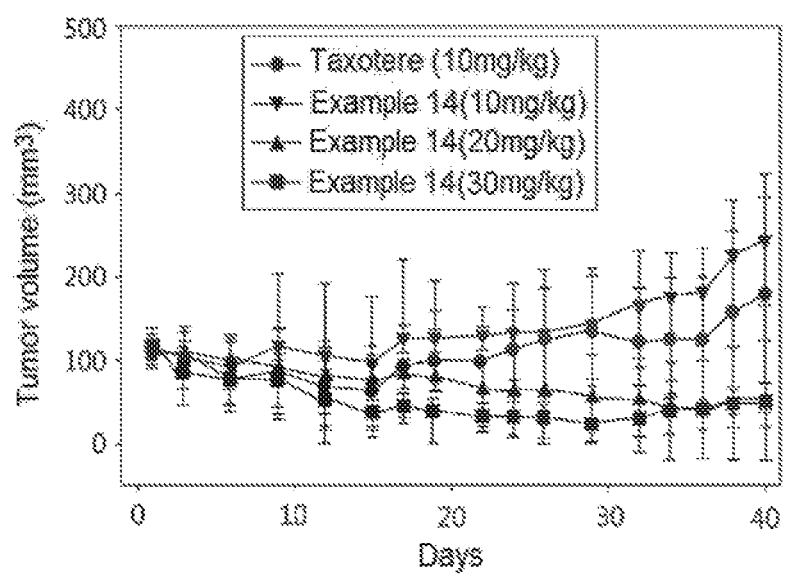
FIG. 12 shows results of the xenograft trials of the polyphosphazene-docetaxel conjugate of Example 14 using BALB/C nude mouse and non-small cell carcinoma A549 cell line.

In order to evaluate the in vivo efficacy of Example 14 compared with Taxotere as reference, nude mouse xenograft trials against gastric cancer cell line MKN-28 were performed using BALB/C nude mouse according to the literature method (Y. J. Jun, et al. Int. J. Pharm. 422 (2012) 374-380). Since the optimal dose of Taxotere is known to be 10 mg/kg, one injection dose of Example 14 was determined to be 10 mg/kg and 20 mg/kg based on the docetaxel content of the polyphosphazene-docetaxel conjugate, which were administered three times (day 1, 5, 9). Both tumor size and body weight of each were measured from the beginning of first injection to 40 days. FIG. 10 displays the antitumor activity against the MKN-28 gastric tumor cells and FIG. 11 shows the body weight changes during the 40 days. It is seen from FIG. 10 that the polyphosphazene-docetaxel conjugate exhibits strong antitumor activity equivalent to Taxotere, and the more important result is seen from FIG. 11 showing that the average body weight of the mice treated with Taxotere is significantly reduced (>10%) during the drug injection period while no significant body weight changes are observed for the conjugate drug, which means that the present conjugate drug shows lower systemic toxicity. The results of xenograft trials performed for non-small cell lung cancer cell line A549 are displayed in FIG. 12 showing that the present conjugate drug exhibits even better antitumor activity than the reference Taxotere.

The invention claimed is:
1. A linear polyphosphazene-drug conjugate compound represented by the following chemical formula 3:

[Chemical formula 3]

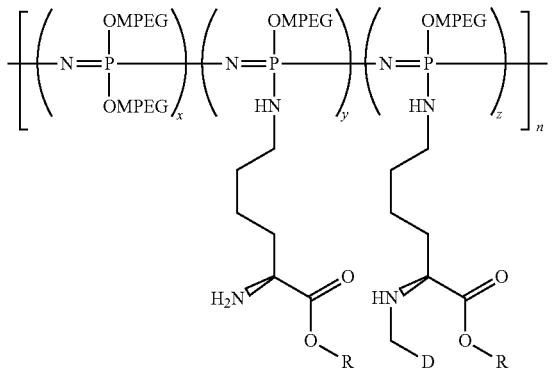

wherein, in chemical formula 3:
  n is independently an integer from 3 to 300;
  MPEG represents methoxy poly(ethylene glycol);
  L is a cis-aconitic acid anhydride linker, which connects a LysEt spacer group to drug molecule D, wherein drug molecule D is docetaxel;
  R is $C_2H_5$;
  x and y are independently in the range of 0 to 0.5;
  z is larger than 0 and less than 1.0; and
  x+y+z=1.

* * * * *